US009708404B2

(12) United States Patent
Lewis et al.

(10) Patent No.: US 9,708,404 B2
(45) Date of Patent: Jul. 18, 2017

(54) ANTI-NTB-A ANTIBODIES AND RELATED COMPOSITIONS AND METHODS

(71) Applicant: Seattle Genetics, Inc., Bothell, WA (US)

(72) Inventors: Timothy S Lewis, Kenmore, WA (US); Che-Leung Law, Shoreline, WA (US)

(73) Assignee: Seattle Genetics, Inc., Bothell, WA (US)

( * ) Notice: Subject to any disclaimer, the term of this patent is extended or adjusted under 35 U.S.C. 154(b) by 0 days.

(21) Appl. No.: 14/758,430

(22) PCT Filed: Dec. 20, 2013

(86) PCT No.: PCT/US2013/077264
§ 371 (c)(1),
(2) Date: Jun. 29, 2015

(87) PCT Pub. No.: WO2014/100740
PCT Pub. Date: Jun. 26, 2014

(65) Prior Publication Data
US 2015/0376276 A1   Dec. 31, 2015

Related U.S. Application Data

(60) Provisional application No. 61/745,239, filed on Dec. 21, 2012.

(51) Int. Cl.
*C07K 16/28* (2006.01)
*A61K 39/00* (2006.01)

(52) U.S. Cl.
CPC .... *C07K 16/2803* (2013.01); *A61K 2039/505* (2013.01); *C07K 2317/20* (2013.01); *C07K 2317/24* (2013.01); *C07K 2317/56* (2013.01); *C07K 2317/565* (2013.01); *C07K 2317/64* (2013.01); *C07K 2317/71* (2013.01); *C07K 2317/73* (2013.01); *C07K 2317/732* (2013.01); *C07K 2317/77* (2013.01); *C07K 2317/92* (2013.01)

(58) Field of Classification Search
CPC .......... C07K 2317/565; C07K 2317/64; C07K 2317/56; C07K 2317/2803
USPC ........... 424/133.1, 172.1; 530/387.3, 388.22, 530/391.7
See application file for complete search history.

(56) References Cited

U.S. PATENT DOCUMENTS

| | | | |
|---|---|---|---|
| 7,115,727 | B2 | 10/2006 | Faris et al. |
| 7,795,412 | B2 | 9/2010 | Goddard et al. |
| 8,609,094 | B2 | 12/2013 | Theuer et al. |
| 8,986,697 | B2 | 3/2015 | Ma et al. |
| 2003/0180888 | A1 | 9/2003 | Fraser |
| 2007/0224198 | A1 | 9/2007 | Blackburn et al. |
| 2009/0181009 | A1* | 7/2009 | Abo ................... C07K 16/2803 424/130.1 |
| 2009/0252747 | A1 | 10/2009 | Faris et al. |
| 2010/0322931 | A1 | 12/2010 | Harding et al. |
| 2011/0171204 | A1* | 7/2011 | Abo ................... C07K 16/2803 424/130.1 |
| 2011/0177972 | A1 | 7/2011 | Chiu et al. |
| 2013/0273077 | A1* | 10/2013 | Abo ................... C07K 16/2803 424/173.1 |
| 2015/0017721 | A1* | 1/2015 | Muller ................. C12N 5/0646 435/375 |
| 2015/0376273 | A1* | 12/2015 | Abo ................... C07K 16/2803 530/387.3 |

FOREIGN PATENT DOCUMENTS

| | | |
|---|---|---|
| EP | 01309339.8 | 7/2002 |
| EP | 02758350.9 | 4/2010 |
| WO | 9517060 | 6/1995 |
| WO | 9636361 | 11/1996 |
| WO | 0153466 | 7/2001 |
| WO | 0190304 | 11/2001 |
| WO | 0155336 | 1/2002 |
| WO | 0179454 | 8/2002 |
| WO | 03055440 | 3/2003 |
| WO | 02024888 | 7/2003 |
| WO | 02072794 | 1/2004 |
| WO | 03008449 | 2/2004 |
| WO | 03068935 | 6/2004 |
| WO | 200516962 | 2/2005 |
| WO | 2004080148 | 3/2005 |
| WO | 03073826 | 4/2005 |
| WO | 2005016962 | 9/2005 |
| WO | 2005031001 | 9/2005 |

(Continued)

OTHER PUBLICATIONS

Lederman et al (Molecular Immunology 28:1171-1181, 1991).*
Li et al (Proc. Natl. Acad. Sci. USA 77:3211-3214, 1980).*
George et al. (Circulation. 1998; 97: 900-906).*
Bottino et al., J. Exp. Med. 194:235-246, 2001.
Korver et al., British Journal of Haematology 137:307-318, 2007.
Falco et al., Eur. J. Immunol. 34:1663-1672, 2004.
Flaig et al., J. Immunol. 172:6524-6527, 2004.
Salort JD. et al., Immunology Letters 129-136, 2011.
Matesanz-Isabel et al., Immunology Letters 104-112, 2011.
Munitz et al., Journal of Immunology 174:110-118, 2005.
Sivori et al., J. Exp. Med. 186: 1129-1136, 1997.
Korver et al. "The lymphoid cell surface receptor NTBA: a novel monoclonal antibody target for leukaemia and lymphoma therapeutics," British Journal of Haematology, vol. 137 pp. 307-319, Apr. 19, 2007.
Valdez et al. "NTBA, a new activating receptor in T-cells that regulates autoimmune disease," J. Biol. Chem., vol. 279, pp. 18662-18669, Feb. 26, 2004.

(Continued)

*Primary Examiner* — Lynn Bristol
(74) *Attorney, Agent, or Firm* — Seattle Genetics, Inc.

(57) ABSTRACT

Disclosed are antibodies, including antibody drug conjugates, that specifically bind to NTB-A. Also disclosed are methods for using the anti-NTB-A antibodies to detect or modulate activity of (e.g., inhibit proliferation of) an NTB-A-expressing cell, as well as for diagnoses or treatment of diseases or disorders (e.g., cancer) associated with NTB-A-expressing cells. Further disclosed is a method of treating multiple myeloma using an anti-NTB-A antibody drug conjugate, which optionally includes an anti-NTB-A antibody as disclosed herein.

12 Claims, 1 Drawing Sheet

(56) References Cited

FOREIGN PATENT DOCUMENTS

| | | |
|---|---|---|
| WO | 2004016733 | 3/2006 |
| WO | 2005019258 | 4/2006 |
| WO | 2005108415 | 5/2006 |
| WO | 2004016734 | 8/2006 |
| WO | 2004016736 | 10/2006 |
| WO | 2004016762 | 1/2007 |
| WO | 2004016799 | 4/2007 |
| WO | 2008027739 | 11/2008 |
| WO | 2009043933 | 4/2009 |
| WO | 2010022737 | 3/2010 |
| WO | 2010115786 | 10/2010 |
| WO | 2011086197 | 6/2011 |
| WO | 2012071411 | 8/2012 |
| WO | 2013008171 | 1/2013 |

OTHER PUBLICATIONS

Shields et al., J. Biological Chemistry. 276:6591-6604, 2001.
Pende et al., J. Exp. Med. 190: 1505-1516, 1999.
Vitale et al., J. Exp. Med. 187: 2065-2072, 1998.
Cao et al., Immunity. 25: 559-570, 2006.
Cocks et al., Nature. 376: 260-263, 1995.
Claus et al., Frontiers in Bioscience. 13: 956-965, 2008.
Eissmann et al., J. Immunol. 177: 3170-3177, 2006.
Kumar et al., Science. 312: 1665-1669, 2006.
Ma et al., Annu. Rev. Immunol. 25: 337-379, 2007.
Stark et al., International Immunology. 18: 241-247, 2006.
Messmer et al., J. Immunol. 176: 4646-4650, 2006.
Tangye et al., Seminars in Immunology. 12: 149-157, 2000.
Yan et al., Proc Acad Nat'l Sci. 104: 10583-10588, 2007.
NCBI Accession No. NP_001171643.1.
NCBI Accession No. NM_001184714.1.

* cited by examiner

SEQUENCE LISTING

```
<160> NUMBER OF SEQ ID NOS: 16

<210> SEQ ID NO 1
<211> LENGTH: 135
<212> TYPE: PRT
<213> ORGANISM: Artificial
<220> FEATURE:
<223> OTHER INFORMATION: Anti-NTB-A mAb Variable Region 11A1 (VH)

<400> SEQUENCE: 1

Met Lys Cys Ser Trp Ile Ile Phe Phe Leu Met Ala Val Val Thr Gly
 1               5                  10                  15

Val Asn Ser Glu Val His Leu Gln Gln Ser Gly Ala Glu Leu Val Lys
            20                  25                  30

Pro Gly Ala Ser Val Lys Leu Ser Cys Thr Ala Ser Gly Phe Asn Ile
        35                  40                  45

Lys Asp Tyr Tyr Val His Trp Val Lys Gln Arg Thr Glu Gln Gly Leu
    50                  55                  60

Glu Trp Ile Gly Lys Ile Asp Pro Glu Asp Gly Glu Ile Lys Tyr Ala
65                  70                  75                  80
```

-continued

```
Pro Lys Phe Gln Gly Glu Ala Thr Ile Thr Ala Asp Thr Ser Ser Asn
                85                  90                  95

Thr Ala Tyr Leu Gln Leu Ser Ser Leu Thr Ser Glu Asp Thr Ala Val
            100                 105                 110

Tyr Tyr Cys Ala Arg Tyr Ser Tyr Phe Asp Tyr Trp Gly Gln Gly
        115                 120                 125

Thr Thr Leu Thr Val Ser Ser
    130                 135

<210> SEQ ID NO 2
<211> LENGTH: 140
<212> TYPE: PRT
<213> ORGANISM: Artificial
<220> FEATURE:
<223> OTHER INFORMATION: Anti-NTB-A mAb Variable Region 11A1 (VL)

<400> SEQUENCE: 2

Met Glu Ser Asn Thr Leu Leu Leu Trp Val Leu Leu Leu Trp Val Pro
1               5                   10                  15

Gly Ser Thr Gly Asp Ile Val Leu Thr Gln Ser Pro Ala Ser Leu Ala
            20                  25                  30

Val Ser Leu Gly Gln Lys Ala Thr Ile Ser Cys Lys Ala Ser Lys Lys
        35                  40                  45

Val Thr Ile Phe Gly Ser Ile Ser Ala Leu His Trp Tyr Gln Gln Lys
    50                  55                  60

Pro Gly Gln Pro Pro Lys Leu Ile Tyr Asn Gly Ala Lys Leu Glu Ser
65                  70                  75                  80

Gly Val Ser Ala Arg Phe Ser Asp Ser Gly Ser Gln Asn Arg Ser Gln
                85                  90                  95

Phe Gly Asn Gln Leu Ser Leu Thr Leu Thr Ile Asp Pro Val Glu Ala
            100                 105                 110

Asp Asp Ala Ala Thr Tyr Tyr Cys Leu Gln Asn Lys Glu Val Pro Tyr
        115                 120                 125

Thr Phe Gly Gly Gly Thr Lys Leu Glu Ile Lys Arg
    130                 135                 140

<210> SEQ ID NO 3
<211> LENGTH: 137
<212> TYPE: PRT
<213> ORGANISM: Artificial
<220> FEATURE:
<223> OTHER INFORMATION: Anti-NTB-A mAb Variable Region 26B7 (VH)

<400> SEQUENCE: 3

Met Gly Trp Ser Tyr Ile Ile Leu Phe Leu Val Ala Thr Ala Thr Gly
1               5                   10                  15

Val His Ser Gln Val Gln Leu Gln Pro Gly Ala Glu Val Val Lys
            20                  25                  30

Pro Gly Thr Ser Val Lys Leu Ser Cys Lys Ala Ser Gly Tyr Asn Phe
        35                  40                  45

Thr Ile Tyr Trp Ile Asn Trp Val Lys Leu Arg Pro Gly Gln Gly Leu
    50                  55                  60

Glu Trp Ile Gly Asp Ile His Pro Gly Arg Gly Asn Thr Asn Leu Asn
65                  70                  75                  80

Glu Lys Phe Lys Thr Lys Ala Thr Leu Thr Val Asp Thr Ser Ser Ser
                85                  90                  95

Thr Ala Tyr Met Gln Leu Asn Ser Leu Ala Phe Glu Asp Ser Ala Leu
```

```
                     100                 105                 110
Tyr Tyr Cys Ala Arg Glu Asp Glu Asp Trp Tyr Phe Asp Val Trp Gly
            115                 120                 125
Ala Gly Thr Thr Val Thr Val Ser Ser
        130                 135
```

<210> SEQ ID NO 4
<211> LENGTH: 128
<212> TYPE: PRT
<213> ORGANISM: Artificial
<220> FEATURE:
<223> OTHER INFORMATION: Anti-NTB-A mAb Variable Region 26B7 (VL)

<400> SEQUENCE: 4

```
Met Lys Leu Leu Ala Glu Leu Gly Leu Leu Leu Phe Cys Phe Ser
1               5                   10                  15

Gly Val Arg Cys Asp Ile Gln Met Asn Gln Ser Pro Ser Ser Leu Ser
                20                  25                  30

Ala Ser Leu Gly Asp Thr Ile Thr Ile Thr Cys Arg Ala Ser Gln Gly
            35                  40                  45

Ile Ser Ile Trp Phe Asn Trp Tyr Gln Gln Lys Ser Gly Asn Ile Pro
        50                  55                  60

Lys Leu Leu Ile Tyr Lys Thr Ser Asn Leu His Thr Gly Val Pro Pro
65                  70                  75                  80

Arg Phe Ser Gly Ser Gly Ser Gly Thr Asp Phe Thr Leu Thr Ile Ser
                85                  90                  95

Ser Leu Gln Pro Glu Asp Ile Ala Thr Tyr Tyr Cys Leu Gln Ser Gln
            100                 105                 110

Ser Tyr Pro Tyr Thr Phe Gly Gly Gly Thr Lys Leu Glu Ile Lys Arg
        115                 120                 125
```

<210> SEQ ID NO 5
<211> LENGTH: 5
<212> TYPE: PRT
<213> ORGANISM: Artificial
<220> FEATURE:
<223> OTHER INFORMATION: CDR Sequence for Anti-NTB-A Antibody VH and VL
      Domain 11A1

<400> SEQUENCE: 5

```
Asp Tyr Tyr Val His
1               5
```

<210> SEQ ID NO 6
<211> LENGTH: 17
<212> TYPE: PRT
<213> ORGANISM: Artificial
<220> FEATURE:
<223> OTHER INFORMATION: CDR Sequence for Anti-NTB-A Antibody VH and VL
      Domain 11A1

<400> SEQUENCE: 6

```
Lys Ile Asp Pro Glu Asp Gly Glu Ile Lys Tyr Ala Pro Lys Phe Gln
1               5                   10                  15

Gly
```

<210> SEQ ID NO 7
<211> LENGTH: 7
<212> TYPE: PRT
<213> ORGANISM: Artificial
<220> FEATURE:
<223> OTHER INFORMATION: CDR Sequence for Anti-NTB-A Antibody VH and VL -continued Domain 11A1

<400> SEQUENCE: 7

Tyr Ser Thr Tyr Phe Asp Tyr
1               5

<210> SEQ ID NO 8
<211> LENGTH: 16
<212> TYPE: PRT
<213> ORGANISM: Artificial
<220> FEATURE:
<223> OTHER INFORMATION: CDR Sequence for Anti-NTB-A Antibody VH and VL
      Domain 11A1

<400> SEQUENCE: 8

Lys Ala Ser Lys Lys Val Thr Ile Phe Gly Ser Ile Ser Ala Leu His
1               5                   10                  15

<210> SEQ ID NO 9
<211> LENGTH: 7
<212> TYPE: PRT
<213> ORGANISM: Artificial
<220> FEATURE:
<223> OTHER INFORMATION: CDR Sequence for Anti-NTB-A Antibody VH and VL
      Domain 11A1

<400> SEQUENCE: 9

Asn Gly Ala Lys Leu Glu Ser
1               5

<210> SEQ ID NO 10
<211> LENGTH: 9
<212> TYPE: PRT
<213> ORGANISM: Artificial
<220> FEATURE:
<223> OTHER INFORMATION: CDR Sequence for Anti-NTB-A Antibody VH and VL
      Domain 11A1

<400> SEQUENCE: 10

Leu Gln Asn Lys Glu Val Pro Tyr Thr
1               5

<210> SEQ ID NO 11
<211> LENGTH: 5
<212> TYPE: PRT
<213> ORGANISM: Artificial
<220> FEATURE:
<223> OTHER INFORMATION: CDR Sequence for Anti-NTB-A Antibody VH and VL
      Domain 26B7

<400> SEQUENCE: 11

Ile Tyr Trp Ile Asn
1               5

<210> SEQ ID NO 12
<211> LENGTH: 17
<212> TYPE: PRT
<213> ORGANISM: Artificial
<220> FEATURE:
<223> OTHER INFORMATION: CDR Sequence for Anti-NTB-A Antibody VH and VL
      Domain 26B7

<400> SEQUENCE: 12

Asp Ile His Pro Gly Arg Gly Asn Thr Asn Leu Asn Glu Lys Phe Lys
1               5                   10                  15
Thr

```
<210> SEQ ID NO 13
<211> LENGTH: 9
<212> TYPE: PRT
<213> ORGANISM: Artificial
<220> FEATURE:
<223> OTHER INFORMATION: CDR Sequence for Anti-NTB-A Antibody VH and VL
      Domain 26B7

<400> SEQUENCE: 13

Glu Asp Glu Asp Trp Tyr Phe Asp Val
1               5

<210> SEQ ID NO 14
<211> LENGTH: 11
<212> TYPE: PRT
<213> ORGANISM: Artificial
<220> FEATURE:
<223> OTHER INFORMATION: CDR Sequence for Anti-NTB-A Antibody VH and VL
      Domain 26B7

<400> SEQUENCE: 14

Arg Ala Ser Gln Gly Ile Ser Ile Trp Phe Asn
1               5                   10

<210> SEQ ID NO 15
<211> LENGTH: 7
<212> TYPE: PRT
<213> ORGANISM: Artificial
<220> FEATURE:
<223> OTHER INFORMATION: CDR Sequence for Anti-NTB-A Antibody VH and VL
      Domain 26B7

<400> SEQUENCE: 15

Lys Thr Ser Asn Leu His Thr
1               5

<210> SEQ ID NO 16
<211> LENGTH: 9
<212> TYPE: PRT
<213> ORGANISM: Artificial
<220> FEATURE:
<223> OTHER INFORMATION: CDR Sequence for Anti-NTB-A Antibody VH and VL
      Domain 26B7

<400> SEQUENCE: 16

Leu Gln Ser Gln Ser Tyr Pro Tyr Thr
1               5
```

US 9,708,404 B2

ANTI-NTB-A ANTIBODIES AND RELATED COMPOSITIONS AND METHODS

CROSS-REFERENCE TO RELATED APPLICATION

This application is the national stage of PCT/US2013/077264 filed Dec. 20, 2013, and claims the benefit of U.S. 61/745,239 filed Dec. 21, 2012, which is incorporated by reference in its entirety for all purposes.

SEQUENCE LISTING

A sequence listing designated NTBA-00111PC-ST25.txt of 8kbytes created Dec. 18, 2013 is incorporated by reference.

BACKGROUND

NTB-A, a single-pass type I membrane glycoprotein also referred to as SLAMF6, is an immunoglobulin superfamily (Ig-SF) member belonging to the CD2/SLAM subfamily. See, e.g., Bottino et al., *J. Exp. Med.* 194:235-246, 2001. NTB-A is characterized, in its extracellular portion, by an N-terminal V-type domain followed by a C2-type domain, while the intracytoplasmic portion contains three tyrosine-based motifs: two immunoreceptor tyrosine-based switch motifs (ITSM; TxYxxV/I) and a classical immunoreceptor tyrosine-based inhibition motif (ITIM; I/V/L/SxYxxL). See id. Through its ITSM motifs, NTB-A associates with the SH2 domain of the SLAM-associated protein SH2D1A and the related Ewing's sarcoma activated transcript (EAT) 2. See Bottino et al., supra; Falco et al., *Eur. J. Immunol.* 34:1663-1672, 2004; Flaig et al., *J. Immunol.* 172:6524-6527, 2004.

NTB-A is expressed on natural killer (NK) cells, NK-like T-cells, T-cells, monocytes, dendritic cells, B-cells, and eosinophils. See Salort JD. et al., *Immunology Letters* 129-136, 2011; Matesanz-Isabel et al., *Immunology Letters* 104-112, 2011; Munitz et al., *Journal of Immunology* 174:110-118, 2005; Bottino et al., *Journal of Experimental Medicine* 194(3):235-246; 2001. NTB-A can function through homotypic interactions (i.e., as a self-ligand), and has been shown to act as a positive regulator of NK cell functions via signaling, inducing NK cell cytotoxicity. See, e.g., See Bottino et al., supra; Falco et al., supra; Flaig et al., supra. NTB-A has also been shown to be expressed on B-cells from chronic lymphocytic leukemia (CLL) and B-cell lymphoma patients. See Korver et al., *British Journal of Haematology* 137:307-318, 2007.

SUMMARY OF THE CLAIMED INVENTION

In one aspect, the present invention provides an isolated antibody that competes for specific binding to human NTB-A with a monoclonal antibody (mAb) comprising VH and VL domains having amino acid sequences as respectively shown in residues 20-135 of SEQ ID NO:1 and residues 21-140 of SEQ ID NO:2.

In another aspect, the present invention provides an isolated murine antibody that specifically binds to human NTB-A and comprises VH and VL domains having amino acid sequences as respectively shown in residues 20-135 of SEQ ID NO:1 and residues 21-140 of SEQ ID NO:2, or a chimeric or humanized form thereof.

In another aspect, the present invention provides an isolated antibody that binds to the same epitope on human NTB-A as a mAb comprising VH and VL domains having amino acid sequences as respectively shown in (i) residues 20-135 of SEQ ID NO:1 and residues 21-140 of SEQ ID NO:2, or (ii) residues 20-137 of SEQ ID NO:3 and residues 21-128 of SEQ ID NO:4.

In yet another aspect, the present invention provides an isolated antibody that specifically binds to human NTB-A and includes (a) a VH domain comprising an amino acid sequence having at least 80% sequence identity with residues 20-135 of SEQ ID NO:1 and a VL domain comprising an amino acid sequence having at least 80% sequence identity with residues 21-140 of SEQ ID NO:2, or (b) a VH domain comprising an amino acid sequence having at least 80% sequence identity with residues 20-137 of SEQ ID NO:3 and a VL domain comprising an amino acid sequence having at least 80% sequence identity with residues 21-128 of SEQ ID NO:4. In some aspects, such antibody comprises 80% identity to the reference sequences and comprises the same CDRs as the reference sequence.

In still another aspect, the present invention provides an isolated antibody that specifically binds to human NTB-A and includes VH and VL domains respectively derived from (a) a VH domain having the amino acid sequence as shown in residues 20-135 of SEQ ID NO:1 and a VL domain having the amino acid sequence as shown in residues 21-140 of SEQ ID NO:2, or (b) a VH domain having the amino acid sequence as shown in residues 20-137 of SEQ ID NO:3 and a VL domain having the amino acid sequence as shown in residues 21-128 of SEQ ID NO:4.

In some embodiments, an antibody of the present invention specifically binds to human NTB-A and comprises the same CDRs as the VH/VL domains having amino acid sequences as respectively shown in residues 20-135 of SEQ ID NO:1 and residues 21-140 of SEQ ID NO:2. For example, in certain embodiments, the antibody comprises CDR-H1, CDR-H2, CDR-H3, CDR-L1, CDR-L2, and CDR-L3 amino acid sequences as respectively shown in SEQ ID NOs:5-10. In other embodiments, the antibody comprises the same CDRs as the VH/VL domains having amino acid sequences as respectively shown in residues 20-137 of SEQ ID NO:3 and residues 21-128 of SEQ ID NO:4. In some such variations, the antibody comprises CDR-H1, CDR-H2, CDR-H3, CDR-L1, CDR-L2, and CDR-L3 amino acid sequences as respectively shown in SEQ ID NOs:11-16.

In other embodiments, an antibody of the present invention specifically binds to human NTB-A and comprises a set of CDRs (CDRs CDR-H1, CDR-H2, CDR-H3, CDR-L1, CDR-L2, and CDR-L3) having three or fewer amino acid substitutions (preferably conservative substitutions) relative to a second set of CDRs, where the second set of CDRs is from the VH/VL domains having the amino acid sequences as respectively shown in (i) residues 20-135 of SEQ ID NO:1 and residues 21-140 of SEQ ID NO:2, or (ii) residues 20-137 of SEQ ID NO:3 and residues 21-128 of SEQ ID NO:4. In particular variations, the second set of CDRs comprises CDR-H1, CDR-H2, CDR-H3, CDR-L1, CDR-L2, and CDR-L3 amino acid sequences as respectively shown in SEQ ID NOs:5-10 or SEQ ID NOs:11-16. In some aspects, the antibody competes for specific binding to human NTB-A with a monoclonal antibody (mAb) comprising VH and VL domains having amino acid sequences as respectively shown in residues 20-135 of SEQ ID NO:1 and residues 21-140 of SEQ ID NO:2.

In certain variations, an antibody of the present invention specifically binds to human NTB-A and is a humanized antibody comprising humanized VH and VL domains. For example, the humanized VH/VL domains may be derived from (i) the VH domain having the amino acid sequence as shown in residues 20-135 of SEQ ID NO:1 and the VL domain having the amino acid sequence as shown in residues 21-140 of SEQ ID NO:2, respectively, or (ii) the VH domain having the amino acid sequence as shown in residues 20-137 of SEQ ID NO:3 and the VL domain having the amino acid sequence as shown in residues 21-128 of SEQ ID NO:4, respectively. In some such embodiments, the humanized antibody comprises the same CDRs as the VH/VL domains specified above. In particular variations, a humanized antibody derived from the VH and VL domains as specified in (i) above comprises CDR-H1, CDR-H2, CDR-H3, CDR-L1, CDR-L2, and CDR-L3 amino acid sequences as respectively shown in SEQ ID NOs:5-10; or a humanized antibody derived from the VH and VL domains as specified in (ii) above comprises CDR-H1, CDR-H2, CDR-H3, CDR-L1, CDR-L2, and CDR-L3 amino acid sequences as respectively shown in SEQ ID NOs:11-16. In other embodiments, the humanized antibody (i) specifically binds to human NTB-A, (ii) comprises a set of CDRs (CDRs CDR-H1, CDR-H2, CDR-H3, CDR-L1, CDR-L2, and CDR-L3) having three or fewer amino acid substitutions (preferably conservative substitutions) relative to a second set of CDRs, where the second set of CDRs is a set of CDRs as specified above (i.e., the second set of CDRs comprises CDR-H1, CDR-H2, CDR-H3, CDR-L1, CDR-L2, and CDR-L3 amino acid sequences as respectively shown in SEQ ID NOs:5-10 and/or SEQ ID NOs:11-16), and (iii) competes for specific binding to human NTB-A with a monoclonal antibody (mAb) comprising VH and VL domains having amino acid sequences as respectively shown in residues 20-135 of SEQ ID NO:1 and residues 21-140 of SEQ ID NO:2.

In some embodiments, an antibody as above further includes at least a portion of an immunoglobulin heavy chain constant region. The immunoglobulin heavy chain constant region may be a natural human constant region or a genetically engineered variant therof, such as, for example, a mutant form of a natural human constant region having reduced binding to an Fcγ receptor relative to the natural human constant region (e.g., a variant having the substitutions E233P, L234V and L235A and/or N297D (numbering according to the EU index as set forth in Kabat)). Suitable heavy chain constant regions include those of human isotypes IgG1, IgG2, IgG3, and IgG4.

In some embodiments, an antibody as above includes a first polypeptide chain comprising the VH domain and a second polypeptide chain comprising the VL domain. In some such variations, the first polypeptide chain further includes at least a portion of an immunoglobulin heavy chain constant region fused to the VH domain, and the second polypeptide chain further includes at least a portion of an immunoglobulin light chain constant region fused to the VL domain. The heavy chain constant region may be a natural human constant region or a genetically engineered variant therof, such as, for example, a mutant form of a natural human constant region having reduced binding to an Fcγ receptor relative to the natural human constant region. Suitable heavy chain constant regions include those of human isotypes IgG1, IgG2, IgG3, and IgG4.

In certain variations, an antibody as above is conjugated to a cytotoxic or cytostatic agent.

In another aspect, the present invention provides an isolated nucleic acid encoding a VH domain and/or VL domain as defined above. The present invention further provides an expression vector comprising a polynucleotide as above, as well as a host cell comprising such an expression vector and which may be used in methods for producing an antibody of the present invention. Such a method for producing an antibody of the invention typically comprises culturing the host cell under conditions in which the antibody is expressed and isolating the antibody from the host cell.

In yet another aspect, the present invention provides a pharmaceutical composition comprising an antibody as above and a pharmaceutically compatible ingredient.

In still another aspect, the present invention provides a method of treating a patient having a cancer characterized by NTB-A expression. The treatment method generally includes administering to the patient an effective regime of an antibody as described above. In certain aspects, the antibody is conjugated to a cytotoxic or cytostatic agent. In some embodiments, the cancer is selected from the group consisting of multiple myeloma, acute myeloid leukemia (AML), and a B-cell lymphoma (e.g., non-Hodgkin's lymphoma (NHL)).

In another aspect, the present invention provides a method of treating a patient having multiple myeloma. The treatment method generally includes administering to the patient an effective regime of an antibody that specifically binds to human NTB-A, where the antibody is conjugated to a cytotoxic or cytostatic agent. In some variations, the anti-NTB-A antibody is an antibody as described above.

These and other aspects of the invention will become evident on reference to the following detailed description of the invention and the attached drawings.

DEFINITIONS

Figure 1:
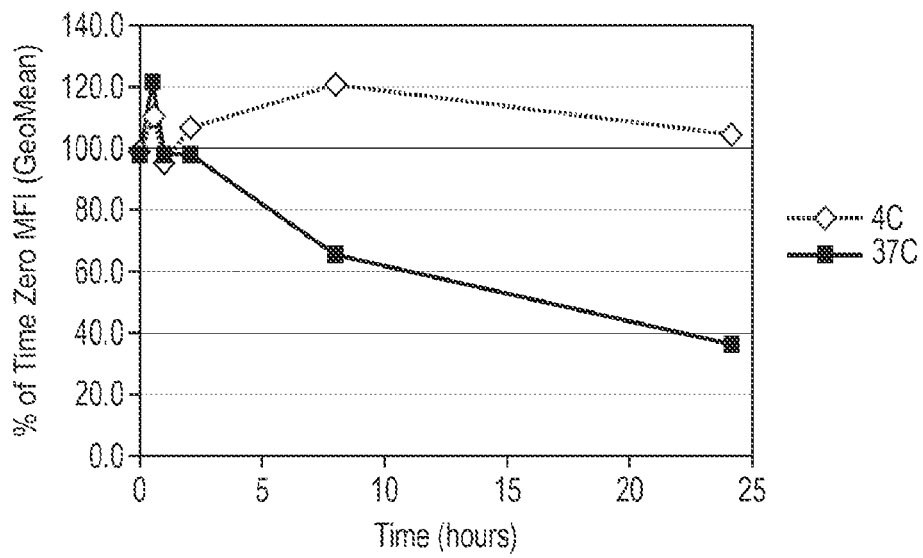
FIG. 1 shows the results of an internalization assay using anti-NTB-A antibody 11A1 on the U-266 multiple myeloma cell line.

Unless defined otherwise, all technical and scientific terms used herein have the same meaning as commonly understood by one of ordinary skill in the art pertinent to the methods and compositions described. As used herein, the following terms and phrases have the meanings ascribed to them unless specified otherwise.

An "antibody-drug conjugate" refers to an antibody conjugated to a cytotoxic agent or cytostatic agent. Typically, antibody-drug conjugates bind to a target antigen (e.g., NTB-A) on a cell surface followed by internalization of the antibody-drug conjugate into the cell and release of the drug.

A "polypeptide" or "polypeptide chain" is a polymer of amino acid residues joined by peptide bonds, whether produced naturally or synthetically. Polypeptides of less than about 10 amino acid residues are commonly referred to as "peptides."

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

The term "antibody" is used herein to denote immunoglobulin proteins produced by the body in response to the presence of an antigen and that bind to the antigen, as well as antigen-binding fragments and engineered variants thereof. Hence, the term "antibody" includes, for example, intact monoclonal antibodies (e.g., antibodies produced using hybridoma technology) and antigen-binding antibody fragments, such as F(ab')$_2$ and Fab fragments. Genetically engineered intact antibodies and fragments, such as chimeric antibodies, humanized antibodies, single-chain Fv fragments, single-chain antibodies, diabodies, minibodies, linear antibodies, multivalent or multispecific (e.g., bispecific) hybrid antibodies, and the like are also included. Thus, the term "antibody" is used expansively to include any protein that comprises an antigen-binding site of an antibody and is capable of specifically binding to its antigen. The term "antibody" also includes an antibody by itself ("naked antibody") or an antibody conjugated to a cytostatic or cytotoxic drug.

The term "genetically engineered antibodies" means antibodies wherein the amino acid sequence has been varied from that of a native antibody. Because of the relevance of recombinant DNA techniques in the generation of antibodies, one need not be confined to the sequences of amino acids found in natural antibodies; antibodies can be redesigned to obtain desired characteristics. The possible variations are many and range from the changing of just one or a few amino acids to the complete redesign of, for example, the variable or constant region. Changes in the constant region will, in general, be made in order to improve or alter characteristics such as, e.g., complement fixation, interaction with cells, and other effector functions. Typically, changes in the variable region will be made in order to improve the antigen-binding characteristics, improve variable region stability, or reduce the risk of immunogenicity.

An "antigen-binding site of an antibody" is that portion of an antibody that is sufficient to bind to its antigen. The minimum such region is typically a variable domain or a genetically engineered variant thereof. Single-domain binding sites can be generated from camelid antibodies (see Muyldermans and Lauwereys, *J. Mol. Recog.* 12:131-140, 1999; Nguyen et al., *EMBO J.* 19:921-930, 2000) or from VH domains of other species to produce single-domain antibodies ("dAbs"; see Ward et al., *Nature* 341:544-546, 1989; U.S. Pat. No. 6,248,516 to Winter et al.). In certain variations, an antigen-binding site is a polypeptide region having only 2 complementarity determining regions (CDRs) of a naturally or non-naturally (e.g., mutagenized) occurring heavy chain variable domain or light chain variable domain, or combination thereof (see, e.g., Pessi et al., *Nature* 362:367-369, 1993; Qiu et al., *Nature Biotechnol.* 25:921-929, 2007). More commonly, an antigen-binding site of an antibody comprises both a heavy chain variable (VH) domain and a light chain variable (VL) domain that bind to a common epitope. Within the context of the present invention, an antibody may include one or more components in addition to an antigen-binding site, such as, for example, a second antigen-binding site of an antibody (which may bind to the same or a different epitope or to the same or a different antigen), a peptide linker, an immunoglobulin constant region, an immunoglobulin hinge, an amphipathic helix (see Pack and Pluckthun, *Biochem.* 31:1579-1584, 1992), a non-peptide linker, an oligonucleotide (see Chaudri et al., *FEBS Letters* 450:23-26, 1999), a cytostatic or cytotoxic drug, and the like, and may be a monomeric or multimeric protein. Examples of molecules comprising an antigen-binding site of an antibody are known in the art and include, for example, Fv, single-chain Fv (scFv), Fab, Fab', F(ab')$_2$, F(ab)c, diabodies, dAbs, minibodies, nanobodies, Fab-scFv fusions, bispecific (scFv)$_4$-IgG, and bispecific (scFv)$_2$-Fab. (See, e.g., Hu et al., *Cancer Res.* 56:3055-3061, 1996; Atwell et al., *Molecular Immunology* 33:1301-1312, 1996; Carter and Merchant, *Curr. Opin. Biotechnol.* 8:449-454, 1997; Zuo et al., *Protein Engineering* 13:361-367, 2000; and Lu et al., *J. Immunol. Methods* 267:213-226, 2002.)

As used herein, the term "immunoglobulin" refers to a protein consisting of one or more polypeptides substantially encoded by immunoglobulin gene(s). One form of immunoglobulin constitutes the basic structural unit of native (i.e., natural) antibodies in vertebrates. This form is a tetramer and consists of two identical pairs of immunoglobulin chains, each pair having one light chain and one heavy chain. In each pair, the light and heavy chain variable regions (VL and VH) are together primarily responsible for binding to an antigen, and the constant regions are primarily responsible for the antibody effector functions. Five classes of immunoglobulin protein (IgG, IgA, IgM, IgD, and IgE) have been identified in higher vertebrates. IgG comprises the major class; it normally exists as the second most abundant protein found in plasma. In humans, IgG consists of four subclasses, designated IgG1, IgG2, IgG3, and IgG4. The heavy chain constant regions of the IgG class are identified with the Greek symbol γ. For example, immunoglobulins of the IgG1 subclass contain a γ1 heavy chain constant region. Each immunoglobulin heavy chain possesses a constant region that consists of constant region protein domains (CH1, hinge, CH2, and CH3; IgG3 also contains a CH4 domain) that are essentially invariant for a given subclass in a species. DNA sequences encoding human and non-human immunoglobulin chains are known in the art. (See, e.g., Ellison et al., *DNA* 1:11-18, 1981; Ellison et al., *Nucleic Acids Res.* 10:4071-4079, 1982; Kenten et al., *Proc. Natl. Acad. Sci. USA* 79:6661-6665, 1982; Seno et al., *Nuc. Acids Res.* 11:719-726, 1983; Riechmann et al., *Nature* 332:323-327, 1988; Amster et al., *Nuc. Acids Res.* 8:2055-2065, 1980; Rusconi and Kohler, *Nature* 314:330-334, 1985; Boss et al., *Nuc. Acids Res.* 12:3791-3806, 1984; Bothwell et al., *Nature* 298:380-382, 1982; van der Loo et al., *Immunogenetics* 42:333-341, 1995; Karlin et al., *J. Mol. Evol.* 22:195-208, 1985; Kindsvogel et al., *DNA* 1:335-343, 1982; Breiner et al., *Gene* 18:165-174, 1982; Kondo et al., *Eur. J. Immunol.* 23:245-249, 1993; and GenBank Accession No. J00228.) For a review of immunoglobulin structure and function see Putnam, *The Plasma Proteins*, Vol V, Academic Press, Inc., 49-140, 1987; and Padlan, *Mol. Immunol.* 31:169-217, 1994. The term "immunoglobulin" is used herein for its common meaning, denoting an intact antibody, its component chains, or fragments of chains, depending on the context.

Full-length immunoglobulin "light chains" (about 25 kDa or 214 amino acids) are encoded by a variable region gene at the amino-terminus (encoding about 110 amino acids) and a by a kappa or lambda constant region gene at the carboxyl-terminus. Full-length immunoglobulin "heavy chains" (about 50 kDa or 446 amino acids) are encoded by a variable region gene (encoding about 116 amino acids) and a gamma, mu, alpha, delta, or epsilon constant region gene (encoding about 330 amino acids), the latter defining the antibody's isotype as IgG, IgM, IgA, IgD, or IgE, respectively. Within light and heavy chains, the variable and constant regions are joined by a "J" region of about 12 or more amino acids, with the heavy chain also including a "D" region of about 10 more amino acids. (See generally Fundamental Immunology (Paul, ed., Raven Press, N.Y., 2nd ed. 1989), Ch. 7).

An immunoglobulin light or heavy chain variable region (also referred to herein as a "light chain variable domain" ("VL domain") or "heavy chain variable domain" ("VH domain"), respectively) consists of a "framework" region interrupted by three hypervariable regions, also called "complementarity determining regions" or "CDRs." The framework regions serve to align the CDRs for specific binding to an epitope of an antigen. Thus, the term "hypervariable region" or "CDR" refers to the amino acid residues of an antibody that are primarily responsible for antigen binding. From amino-terminus to carboxyl-terminus, both VL and VH domains comprise the following framework (FR) and CDR regions: FR1, CDR1, FR2, CDR2, FR3, CDR3, FR4. The assignment of amino acids to each domain is in accordance with the definitions of Kabat, *Sequences of Proteins of Immunological Interest* (National Institutes of Health, Bethesda, Md., 1987 and 1991), or Chothia & Lesk, *J. Mol. Biol.* 196:901-917, 1987; Chothia et al., *Nature* 342:878-883, 1989. Kabat also provides a widely used numbering convention (Kabat numbering) in which corresponding residues between different heavy chains or between different light chains are assigned the same number. CDRs 1, 2, and 3 of a VL domain are also referred to herein, respectively, as CDR-L1, CDR-L2, and CDR-L3; CDRs 1, 2, and 3 of a VH domain are also referred to herein, respectively, as CDR-H1, CDR-H2, and CDR-H3.

Unless the context dictates otherwise, the term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

An immunoglobulin VH or VL domain "derived from" a reference variable domain means a genetically engineered VH or VL domain comprising some or all CDRs entirely or substantially from the reference variable domain. In some variations, the derived variable domain is a humanized VH or VL domain. An antibody comprising a VH or VL domain "derived from" a reference variable domain will typically retain binding characteristics of an antibody comprising the reference variable domain.

The term "humanized VH domain" or "humanized VL domain" refers to an immunoglobulin VH or VL domain comprising some or all CDRs entirely or substantially from a non-human donor immunoglobulin (e.g., a mouse or rat) and variable domain framework sequences entirely or substantially from human immunoglobulin sequences. The non-human immunoglobulin providing the CDRs is called the "donor" and the human immunoglobulin providing the framework is called the "acceptor." In some instances, humanized antibodies will retain some non-human residues within the human variable domain framework regions to enhance proper binding characteristics (e.g., mutations in the frameworks may be required to preserve binding affinity when an antibody is humanized).

A "humanized antibody" is an antibody comprising one or both of a humanized VH domain and a humanized VL domain. Immunoglobulin constant region(s) need not be present, but if they are, they are entirely or substantially from human immunoglobulin constant regions.

A CDR in a humanized antibody is "substantially from" a corresponding CDR in a non-human antibody when at least 60%, at least 85%, at least 90%, at least 95% or 100% of corresponding residues (as defined by Kabat) are identical between the respective CDRs. In particular variations of a humanized VH or VL domain in which CDRs are substantially from a non-human immunoglobulin, the CDRs of the humanized VH or VL domain have no more than six (e.g., no more than five, no more than four, no more than three, no more than two, or nor more than one) amino acid substitutions (preferably conservative substitutions) across all three CDRs relative to the corresponding non-human VH or VL CDRs. The variable region framework sequences of an antibody VH or VL domain or, if present, a sequence of an immunoglobulin constant region, are "substantially from" a human VH or VL framework sequence or human constant region, respectively, when at least about 80%, at least 85%, at least 90%, at least 95%, or 100% of corresponding residues defined by Kabat are identical. Hence, all parts of a humanized antibody, except the CDRs, are entirely or substantially from corresponding parts of natural human immunoglobulin sequences.

Antibodies are typically provided in isolated form. This means that an antibody is typically at least 50% w/w pure of interfering proteins and other contaminants arising from its production or purification but does not exclude the possibility that the antibody is combined with an excess of pharmaceutical acceptable carrier(s) or other vehicle intended to facilitate its use. Sometimes antibodies are at least 60%, 70%, 80%, 90%, 95 or 99% w/w pure of interfering proteins and contaminants from production or purification.

Specific binding of an antibody to its target antigen means an affinity of at least $10^6$, $10^7$, $10^8$, $10^9$, or $10^{10}$ $M^{-1}$. Specific binding is detectably higher in magnitude and distinguishable from non-specific binding occurring to at least one unrelated target. Specific binding can be the result of formation of bonds between particular functional groups or particular spatial fit (e.g., lock and key type) whereas nonspecific binding is usually the result of van der Waals forces.

The term "epitope" refers to a site on an antigen to which an antibody binds. An epitope can be formed from contiguous amino acids or noncontiguous amino acids juxtaposed by tertiary folding of one or more proteins. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., *Epitope Mapping Protocols, in Methods in Molecular Biology*, Vol. 66, Glenn E. Morris, Ed. (1996).

Antibodies that recognize the same or overlapping epitopes can be identified in a simple immunoassay showing the ability of one antibody to compete with the binding of another antibody to a target antigen. The epitope of an antibody can also be defined by X-ray crystallography of the antibody bound to its antigen to identify contact residues. Alternatively, two antibodies have the same epitope if all amino acid mutations in the antigen that reduce or eliminate binding of one antibody reduce or eliminate binding of the other (provided that such mutations do not produce a global alteration in antigen structure). Two antibodies have overlapping epitopes if some amino acid mutations that reduce or eliminate binding of one antibody reduce or eliminate binding of the other.

Competition between antibodies is determined by an assay in which an antibody under test inhibits specific binding of a reference antibody to a common antigen (see, e.g., Junghans et al., *Cancer Res.* 50:1495, 1990). A test antibody competes with a reference antibody if an excess of a test antibody (e.g., at least 2×, 5×, 10×, 20× or 100×) inhibits binding of the reference antibody by at least 55% but preferably 75%, 90% or 99% as measured in a competitive binding assay. Antibodies identified by competition assay (competing antibodies) include antibodies binding to the same epitope as the reference antibody and antibodies binding to an adjacent epitope sufficiently proximal to the epitope bound by the reference antibody for steric hindrance to occur. Antibodies identified by competition assay also include those that indirectly compete with a reference antibody by causing a conformational change in the target protein thereby preventing binding of the reference antibody to a different epitope than that bound by the test antibody.

The terms "expression unit" and "expression cassette" are used interchangeably herein and denote a nucleic acid segment encoding a polypeptide of interest and capable of providing expression of the nucleic acid segment in a host cell. An expression unit typically comprises a transcription promoter, an open reading frame encoding the polypeptide of interest, and a transcription terminator, all in operable configuration. In addition to a transcriptional promoter and terminator, an expression unit may further include other nucleic acid segments such as, e.g., an enhancer or a polyadenylation signal.

The term "expression vector," as used herein, refers to a nucleic acid molecule, linear or circular, comprising one or more expression units. In addition to one or more expression units, an expression vector may also include additional nucleic acid segments such as, for example, one or more origins of replication or one or more selectable markers. Expression vectors are generally derived from plasmid or viral DNA, or may contain elements of both.

With regard to proteins as described herein, reference to amino acid residues corresponding to those specified by SEQ ID NO includes post-translational modifications of such residues.

The term "patient" includes human and other mammalian subjects that receive either prophylactic or therapeutic treatment.

The term "effective amount," in the context of treatment of a NTB-A-expressing disorder by administration of an anti-NTB-A antibody as described herein, refers to an amount of such antibody that is sufficient to inhibit the occurrence or ameliorate one or more symptoms of the NTB-A-expressing disorder. An effective amount of an antibody is administered according to the methods of the present invention in an "effective regime." The term "effective regime" refers to a combination of amount of the antibody being administered and dosage frequency adequate to accomplish prophylactic or therapeutic treatment of the disorder.

For purposes of classifying amino acids substitutions as conservative or nonconservative, the following amino acid substitutions are considered conservative substitutions: serine substituted by threonine, alanine, or asparagine; threonine substituted by proline or serine; asparagine substituted by aspartic acid, histidine, or serine; aspartic acid substituted by glutamic acid or asparagine; glutamic acid substituted by glutamine, lysine, or aspartic acid; glutamine substituted by arginine, lysine, or glutamic acid; histidine substituted by tyrosine or asparagine; arginine substituted by lysine or glutamine; methionine substituted by isoleucine, leucine or valine; isoleucine substituted by leucine, valine, or methionine; leucine substituted by valine, isoleucine, or methionine; phenylalanine substituted by tyrosine or tryptophan; tyrosine substituted by tryptophan, histidine, or phenylalanine; proline substituted by threonine; alanine substituted by serine; lysine substituted by glutamic acid, glutamine, or arginine; valine substituted by methionine, isoleucine, or leucine; and tryptophan substituted by phenylalanine or tyrosine. Conservative substitutions can also mean substitutions between amino acids in the same class. Classes are as follows: Group I (hydrophobic side chains): met, ala, val, leu, ile; Group II (neutral hydrophilic side chains): cys, ser, thr; Group III (acidic side chains): asp, glu; Group IV (basic side chains): asn, gln, his, lys, arg; Group V (residues influencing chain orientation): gly, pro; and Group VI (aromatic side chains): trp, tyr, phe.

Two amino acid sequences have "100% amino acid sequence identity" if the amino acid residues of the two amino acid sequences are the same when aligned for maximal correspondence. Sequence comparisons can be performed using standard software programs such as those included in the LASERGENE bioinformatics computing suite, which is produced by DNASTAR (Madison, Wisconsin). Other methods for comparing two nucleotide or amino acid sequences by determining optimal alignment are well-known to those of skill in the art. (See, e.g., Peruski and Peruski, *The Internet and the New Biology: Tools for Genomic and Molecular Research* (ASM Press, Inc. 1997); Wu et al. (eds.), "Information Superhighway and Computer Databases of Nucleic Acids and Proteins," in *Methods in Gene Biotechnology* 123-151 (CRC Press, Inc. 1997); Bishop (ed.), *Guide to Human Genome Computing* (2nd ed., Academic Press, Inc. 1998).) Two amino acid sequences are considered to have "substantial sequence identity" if the two sequences have at least 80%, at least 85%, at least 90%, or at least 95% sequence identity relative to each other.

Percentage sequence identities are determined with antibody sequences maximally aligned by the Kabat numbering convention. After alignment, if a subject antibody region (e.g., the entire variable domain of a heavy or light chain) is being compared with the same region of a reference antibody, the percentage sequence identity between the subject and reference antibody regions is the number of positions occupied by the same amino acid in both the subject and reference antibody region divided by the total number of aligned positions of the two regions, with gaps not counted, multiplied by 100 to convert to percentage.

Compositions or methods "comprising" one or more recited elements may include other elements not specifically recited. For example, a composition that comprises antibody may contain the antibody alone or in combination with other ingredients.

Designation of a range of values includes all integers within or defining the range.

An antibody effector function refers to a function contributed by an Fc region of an Ig. Such functions can be, for example, antibody-dependent cellular cytotoxicity, antibody-dependent cellular phagocytosis, or complement-dependent cytotoxicity. Such function can be effected by, for example, binding of an Fc region to an Fc receptor on an immune cell with phagocytic or lytic activity or by binding of an Fc region to components of the complement system. Typically, the effect(s) mediated by the Fc-binding cells or complement components result in inhibition and/or depletion of the NTB-A-targeted cell. Fc regions of antibodies can recruit Fc receptor (FcR)-expressing cells and juxtapose them with antibody-coated target cells. Cells expressing surface FcR for IgGs including FcγRIII (CD16), FcγRII (CD32) and FcγRIII (CD64) can act as effector cells for the destruction of IgG-coated cells. Such effector cells include monocytes, macrophages, natural killer (NK) cells, neutrophils and eosinophils. Engagement of FcγR by IgG activates antibody-dependent cellular cytotoxicity (ADCC) or antibody-dependent cellular phagocytosis (ADCP). ADCC is mediated by CD16$^+$ effector cells through the secretion of membrane pore-forming proteins and proteases, while phagocytosis is mediated by CD32$^+$ and CD64$^+$ effector cells (see *Fundamental Immunology*, 4$^{th}$ ed., Paul ed., Lippincott-Raven, N.Y., 1997, Chapters 3, 17 and 30; Uchida et al., *J. Exp. Med.* 199:1659-69, 2004; Akewanlop et al., *Cancer Res.* 61:4061-65, 2001; Watanabe et al., *Breast Cancer Res. Treat.* 53:199-207, 1999). In addition to ADCC and ADCP, Fc regions of cell-bound antibodies can also activate the complement classical pathway to elicit complement-dependent cytotoxicity (CDC). C1q of the complement system binds to the Fc regions of antibodies when they are complexed with antigens. Binding of C1q to cell-bound antibodies can initiate a cascade of events involving the proteolytic activation of C4 and C2 to generate the C3 convertase. Cleavage of C3 to C3b by C3 convertase enables the activation of terminal complement components including C5b, C6, C7, C8 and C9. Collectively, these proteins form membrane-attack complex pores on the antibody-coated cells. These pores disrupt the cell membrane integrity, killing the target cell (see *Immunobiology*, 6$^{th}$ ed., Janeway et al., Garland Science, N. Y., 2005, Chapter 2).

The term "antibody-dependent cellular cytotoxicity," or "ADCC," is a mechanism for inducing cell death that depends on the interaction of antibody-coated target cells with immune cells possessing lytic activity (also referred to as effector cells). Such effector cells include natural killer cells, monocytes/macrophages and neutrophils. The effector cells attach to an Fc region of Ig bound to target cells via their antigen-combining sites. Death of the antibody-coated target cell occurs as a result of effector cell activity.

The term "antibody-dependent cellular phagocytosis," or "ADCP," refers to the process by which antibody-coated cells are internalized, either in whole or in part, by phagocytic immune cells (e.g., macrophages, neutrophils and dendritic cells) that bind to an Fc region of Ig.

The term "complement-dependent cytotoxicity," or "CDC," refers to a mechanism for inducing cell death in which an Fc region of a target-bound antibody activates a series of enzymatic reactions culminating in the formation of holes in the target cell membrane. Typically, antigen-antibody complexes such as those on antibody-coated target cells bind and activate complement component C1q which in turn activates the complement cascade leading to target cell death. Activation of complement may also result in deposition of complement components on the target cell surface that facilitate ADCC by binding complement receptors (e.g., CR3) on leukocytes.

A "cytotoxic effect" refers to the depletion, elimination and/or the killing of a target cell. A "cytotoxic agent" refers to an agent that has a cytotoxic effect on a cell. Cytotoxic agents can be conjugated to an antibody or administered in combination with an antibody.

A "cytostatic effect" refers to the inhibition of cell proliferation. A "cytostatic agent" refers to an agent that has a cytostatic effect on a cell, thereby inhibiting the growth and/or expansion of a specific subset of cells. Cytostatic agents can be conjugated to an antibody or administered in combination with an antibody.

The term "pharmaceutically acceptable" means approved or approvable by a regulatory agency of the Federal or a state government or listed in the U.S. Pharmacopeia or other generally recognized pharmacopeia for use in animals, and more particularly in humans. The term "pharmaceutically compatible ingredient" refers to a pharmaceutically acceptable diluent, adjuvant, excipient, or vehicle with which an anti-NTB-A antibody is formulated.

The phrase "pharmaceutically acceptable salt," refers to pharmaceutically acceptable organic or inorganic salts of an anti-NTB-A antibody or conjugate thereof or agent administered with an anti-NTB-A antibody. Exemplary salts include sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p toluenesulfonate, and pamoate (i.e., 1,1' methylene bis -(2 hydroxy 3 naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counterion.

Unless otherwise apparent from the context, when a value is expressed as "about" X or "approximately" X, the stated value of X will be understood to be accurate to ±10%.

Glycosylation depends on the host cell used to express the antibody. Because the cell type used for expression of recombinant antibodies as potential therapeutics is rarely the native cell, significant variations in the glycosylation pattern of the antibodies can occur between recombinantly expressed antibodies in nonnative cells and antibodies of the same primary heavy and light chain sequences expressed in their native cells. Mammalian cell lines of rodent origin (such as SP2/0, CHO or BHK) are able to confer a glycosylation that has some similarity to a human glycosylation. However, some human components may be missing (such as the 2,6-linked sialylation) and a number of other components not usually found in humans may be present, such as terminals sialic acids that do not usually exist in human cells (NeuGc, for example) or terminal galactose linked to another galactose in a way that is usually absent from human cells (Gal-Gal structures). Recombinant IgGs expressed in CHO cells are generally less galactosylated compared to the recombinant immunoglobulins expressed in mouse myeloma cells. Accordingly, recombinant IgGs produced in CHO cells may contain higher levels of G0 glycans compared with rIgGs produced in mouse myeloma cell lines.

The glycosylation structure of antibodies can be analyzed by conventional techniques of carbohydrate analysis, including lectin chromatography, NMR, Mass spectrometry, HPLC, gel permeation chromatography, monosaccharide compositional analysis, sequential enzymatic digestion, and High-Performance Anion-Exchange Chromatography with Pulsed Amperometric Detection, which uses high pH anion exchange chromatography to separate oligosaccharides based on charge. Methods for releasing oligosaccharides for analytical purposes include enzymatic treatment (commonly performed using peptide-N-glycosidase F/endo-.beta.-galactosidase), elimination using harsh alkaline environment to release mainly O-linked structures, and chemical methods using anhydrous hydrazine to release both N- and O-linked oligosaccharides.

Thus, the glycosylation pattern of a recombinantly expressed antibody can be characteristic of the cell type in which expression is performed (e.g., CHO) and distinguishable different by any of the above techniques from other cell types particularly cells of other species, such as mouse and human.

DETAILED DESCRIPTION

I. General

The present invention provides antibodies that specifically bind to NTB-A. The antibodies are useful, e.g., for treatment and diagnoses of various NTB-A-expressing cancers, as well as for detecting NTB-A (e.g., detection of NTB-A expression on cells). Methods for such treatment, diagnoses, and NTB-A detection using antibodies of the invention are also provided.

The present invention also provides a method of treating multiple myeloma using an antibody-drug conjugate (ADC) that specifically binds to NTB-A. It is believed that the present inventors are the first to demonstrate killing of multiple myeloma cells using an anti-NTB-A ADC Anti-NTB-A ADCs for treating multiple myeloma may include, for example, ADCs comprising an anti-NTB-A antibody as described herein. In one aspect, the method comprises administering to a patient in need thereof an antibody that specifically binds to human NTB-A, wherein the antibody is conjugated to a cytotoxic agent.

II. Target Molecules

Unless otherwise indicated, NTB-A means a human NTB-A. An exemplary human sequence is assigned UniProtKB/Swiss-Prot accession number Q96DU3. Four splice-variant isoforms are known. The mature extracellular region is bounded by residues 22-226 of Q96DU3.

Unless otherwise apparent from the context, reference to NTB-A means at least an extracellular domain of the protein and usually the complete protein other than a cleavable signal peptide (amino acids 1-21 of Q96DU3).

III. Antibodies of the Invention

In one aspect, the present invention provides isolated anti-NTBA antibodies that specifically bind to an epitope of the mature NTB-A extracellular region (e.g., an epitope residing within amino acid residues 22-226 of UniProtKB/Swiss-Prot accession number Q96DU3). In certain embodiments, an anti-NTB-A antibody in accordance with the present invention is capable of competing for binding to human NTB-A antigen with a monoclonal antibody having the same VH/VL domains as an anti-NTB-A mAb identified and isolated by the present inventors. In certain aspects, anti-NTB-A antibody in accordance with the present invention is a murine antibody as identified herein or a chimeric or humanized form thereof.

One method of measuring affinity of an antibody for its target antigen is by determining an antibody's apparent dissociation constant. In some aspects, the antibodies described herein have an apparent disassociation constant (kd) for NTB-A within a range of 0.1 nM to 10 nM, preferably 0.1 nM to 5 nM, more preferably 0.1 nM to 2 nM or 0.1 nM to 1 nM.

A mouse anti-NTB-A monoclonal antibody, designated as mAb 11A1, was identified and characterized. The murine 11A1 antibody is an IgG1 antibody. MAb 11A1 was found to bind to the full-length extracellular region of NTB-A (residues 22-226 of UniProtKB/Swiss-Prot accession number Q96DU3) with a kd of 0.13 nM, but not to NTB-A isoform 4, (missing residues 18-128 of accession number Q96DU3). A second antibody, designated as mAb 26B7, was also identified and characterized. MAb 26B7 was found to compete with mAb 11A1 for binding to human NTB-A in a competitive binding assay (see Example 5) and bound to NTB-A with a kd of 0.16 nM. The VH, VL, and VH/VL Kabat CDR amino acid sequences for each of murine mAbs 11A1 and 26B7 were determined and are depicted below in Tables 1 and 2. The 11A1 and 26B7 antibodies do not bind to cynomolgus monkey NTB-A.

TABLE 1

Anti-NTB-A mAb Variable Region Amino Acid Sequences

| mAb (VH/VL) | Amino Acid Sequence†‡ | SEQ ID NO: |
|---|---|---|
| 11A1 (VH) | mkcswiifflmavvtgvnsevhlqqsgaelvkpgasvkl sctasgfnikdyyvhwvkqrteqglewigkidpedgeik yapkfqgeatitadtssntaylqlssltsedtavyycar ystyfdywgqgttltvss | 1 |
| 11A1 (VL) | mesntlllwvlllwvpqstqdivltqspaslavslgqka tisckaskkvtifgsisalhwyqqkpgqppkliyngakl esgvsarfsdsgsqnrsqfgnqlsltltidpveaddaat yyclqnkevpytfgggtkleikr | 2 |
| 26B7 (VH) | mqwsyiilflvatatqvhsqvqllqpgaevvkpgtsvkl sckasgynftiywinwvklrpgqglewigdihpgrgntn lnekfktkatltvdtssstaymqlnslafedsalyycar ededwyfdvwgagttvtvss | 3 |
| 26B7 (VL) | mkllaellgllllfcfsgvrcdiqmnqspsslsaslgdti titcrasqgisiwfnwyqqksgnipklliyktsnlhtgv pprfsgsgsgtdftltisslqpediatyyclqsqsypyt fgggtkleikr | 4 |

†Amino acid sequences shown include the N-terminal signal peptide (underlined). Reference herein to VH and VL domains for these mAbs are to the mature polypeptide (and thus do not include the signal peptide), unless the context clearly indicates otherwise.
‡Kabat CDRs are shown in bold.

Accordingly, in certain embodiments, the present invention provides an isolated murine comprising (i) a VH domain having the amino acid sequence as shown in residues 20-135 of SEQ ID NO:1 and (ii) a VL domain having the amino acid sequence as shown in residues 21-140 of SEQ ID NO:2, or a chimeric or humanized form thereof. As with the murine antibody, the chimeric and humanized forms thereof bind human NTB-A, but not cynomolgus monkey NTB-A.

In certain embodiments, the present invention provides an isolated antibody that competes for specific binding to human NTB-A with a monoclonal antibody (mAb) comprising (i) a VH domain having the amino acid sequence as shown in residues 20-135 of SEQ ID NO:1 and (ii) a VL domain having the amino acid sequence as shown in residues 21-140 of SEQ ID NO:2.

The present invention further provides an isolated antibody that specifically binds to the same epitope of human NTB-A as a mAb comprising (a) a VH domain having the amino acid sequence as shown in residues 20-135 of SEQ ID NO:1 and a VL domain having the amino acid sequence as shown in residues 21-140 of SEQ ID NO:2 or (b) a VH domain having the amino acid sequence as shown in residues 20-137 of SEQ ID NO:3 and a VL domain having the amino acid sequence as shown in residues 21-128 of SEQ ID NO:4. In certain variations, the antibody binds to the same epitope of NTB-A as the aforementioned mAb as determined by an epitope mapping method selected from (i) X-ray co-crystallography, (ii) array-based oligo-peptide scanning (also sometimes referred to as overlapping peptide scan or pepscan analysis), (iii) site-directed mutagenesis (e.g., alanine scanning mutagenesis), and (iv) H/D exchange mass spectrometry. These epitope mapping methods are well-known in the art and may be readily used in accordance with the present invention.

The present invention also provides an isolated antibody that specifically binds to human NTB-A and includes (i) a VH domain comprising an amino acid sequence having at least 80% sequence identity with residues 20-135 of SEQ ID NO:1 or 20-137 of SEQ ID NO:3; and/or (ii) a VL domain comprising an amino acid sequence having at least 80% sequence identity with residues 21-140 of SEQ ID NO:2 or 21-128 of SEQ ID NO:4. Typically, where the antibody includes both a heavy chain variable domain and a light chain variable domain, the VH and VL domains correspond to the same reference antibody from Table 1 (i.e., the VH and VL domains typically have specified sequence identities with residues 20-135 of SEQ ID NO:1 and 21-140 of SEQ ID NO:2, respectively, or with residues 20-137 of SEQ ID NO:3 and 21-128 of SEQ ID NO:4, respectively).

The present invention still further provides an isolated antibody that specifically binds to human NTB-A and includes (i) a VH domain derived from a VH domain having the amino acid sequence as shown in residues 20-135 of SEQ ID NO:1 or 20-137 of SEQ ID NO:3, and/or (ii) a VL domain derived from a VL domain having the amino acid sequence as shown in residues 21-140 of SEQ ID NO:2 or 21-128 of SEQ ID NO:4. For example, the VH and/or VL domains may be respectively derived from (a) a VH domain having the amino acid sequence as shown in residues 20-135 of SEQ ID NO:1 and/or a VL domain having the amino acid sequence as shown in residues 21-140 of SEQ ID NO:2, or (b) a VH domain having the amino acid sequence as shown in residues 20-137 of SEQ ID NO:3 and/or a VL domain having the amino acid sequence as shown in residues 21-128 of SEQ ID NO:4. The variable domain framework sequences of the derived VH or VL domain may be entirely or substantially from an immunoglobulin sequence different from that of the reference sequence such as, for example, an immunoglobulin sequence from a different species (e.g., human). Thus, in certain embodiments, the present invention provides a humanized antibody comprising one or both of a humanized VH domain and a humanized VL domain derived from one or both of the VH and VL domains specified in (a) or (b) above, as further described herein. Typically, but not always, humanized antibodies will retain some non-human residues from the donor species within the human variable domain framework regions.

The present invention still further provides a monoclonal antibody that specifically binds to NTB-A and comprises complementary determining region (CDR) sequences as set forth in SEQ ID NO:5 (CDR1), SEQ ID NO:6 (CDR2), and SEQ ID NO:7 (CDR3), and light chain CDR sequences as set forth in SEQ ID NO:8 (CDR4), SEQ ID NO:9 (CDR5), and SEQ ID NO:10 (CDR6) and having 0, 1, 2 or 3 conservative amino acid substitutions in each CDR. In some aspects, the antibody is a humanized monoclonal antibody. In some aspects, there are 0 or 1 conservative amino acid substitutions in each CDR. Such an antibody can be for example, mouse, chimeric, humanized or veneered.

The present invention still further provides a monoclonal antibody that specifically binds to NTB-A and comprises complementary determining region (CDR) sequences as set forth in SEQ ID NO:11 (CDR1), SEQ ID NO:12 (CDR2), and SEQ ID NO:13 (CDR3), and light chain CDR sequences as set forth in SEQ ID NO:14 (CDR4), SEQ ID NO:15 (CDR5), and SEQ ID NO:16 (CDR6) and having 0, 1, 2 or 3 conservative amino acid substitutions in each CDR. In some aspects, the antibody is a humanized monoclonal antibody. Such an antibody can be for example, mouse, chimeric, humanized or veneered.

The antibodies of the present invention may be assayed for specific binding by any method known in the art. The immunoassays which can be used include, but are not limited to, assay systems using techniques such as western blots, radioimmunoassays, ELISA, "sandwich" immunoassays, immunoprecipitation assays, precipitin assays, gel diffusion precipitin assays, immunoradiometric assays, fluorescent immunoassays, protein A immunoassays, and complement-fixation assays. Such assays are routine and well-known in the art (see, e.g., Ausubel et al., eds, 1994, *Current Protocols in Molecular Biology*, Vol. 1, John Wiley & sons, Inc., New York). Routine assays such as those described in *Antibodies, A Laboratory Manual* (Cold Spring Harbor Laboratory, Ed Harlow and David Lane, 1988) can also be performed. Additionally, the BIACORE® (GE Healthcare, Piscataway, N.J.) is only one of a variety of surface plasmon resonance assay formats that are routinely used for binding analysis of monoclonal antibodies. Other references, e.g., *The Epitope Mapping Protocols, Methods in Molecular Biology*, Vol. 66 (Glenn Morris ed. Humana Press, 1996), describe alternative methods that could be used to bind antibodies and would be expected to provide comparable information regarding the binding specificity of the antibodies to NTB-A.

To evaluate whether an antibody competes for specific binding to human NTB-A with a mAb comprising the VH and VL domains of the 11A1 mAb (i.e., a VH domain having the amino acid sequence as shown in residues 20-135 of SEQ ID NO:1 and a VL domain having the amino acid sequence as shown in residues 21-140 of SEQ ID NO:2), a competitive binding assay as follows is used.

Figure 2:
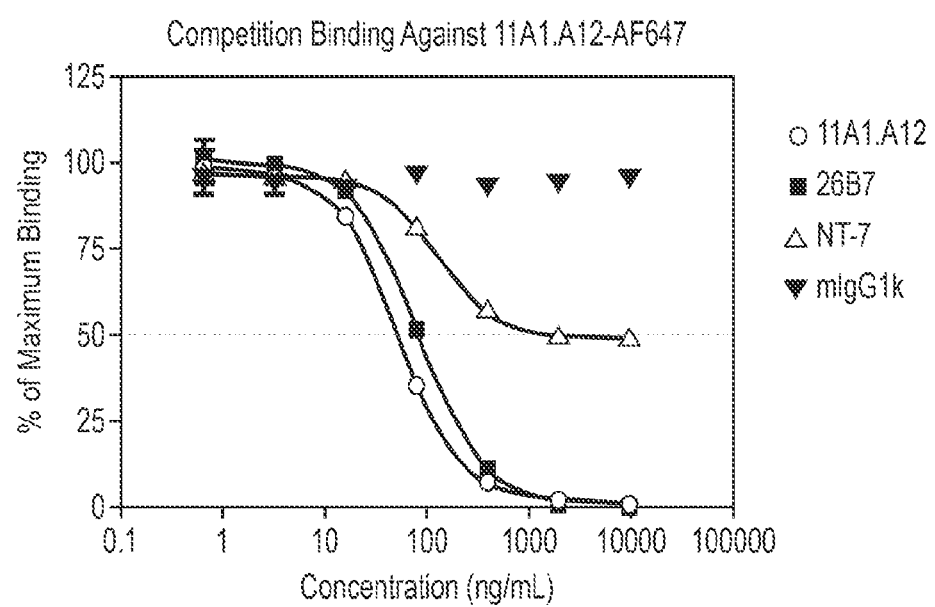
FIG. 2 shows the results of an antibody competition assay using anti-NTB-A antibodies 11A1 and 26B7.

This assay utilizes a "reference antibody" comprising the 11A1 murine IgG1 antibody (i.e., the 11A1 VH and VL domains in the bivalent structure of a native antibody). NTB-A positive Ramos cells are plated at $2\times10^5$ cells per well in a 96 well V-bottom plate (Thermo Scientific, Rochester, N.Y.). Five-fold serial dilutions of 2× concentrated antibodies (20 µg/ml is the 2× starting concentration unlabeled sample antibodies) are prepared in FACs buffer (PBS+ 2% fetal bovine serum+0.02% sodium azide) containing a 2× constant concentration of AF647 labeled 11A1 murine antibody at 2× its Kd value of 0.0188 µg/mL (0.0376 µg/mL). The antibody solutions are incubated with cells for 1 hour on ice, protected from light. The cells are washed twice with FACs buffer and analyzed on the LSRII flow cytometer (BD BioSciences, San Jose, Calif.). Data are presented as percent of maximum binding. The sample antibody "competes with" the labeled reference antibody for specific binding to NTB-A if the sample antibody reduces the reference antibody's binding to NTB-A to levels less than 45% of maximum binding (i.e., 0 to 45%) at a concentration of 10 µg/ml of unlabeled sample antibody. In some aspects, an antibody competes for binding if the sample antibody reduces the reference antibody's binding to NTB-A to levels less than 30% of maximum binding at a concentration of 10 µg/ml of unlabeled sample antibody. In some aspects, an antibody competes for binding if the sample antibody reduces the reference antibody's binding to NTB-A to levels less than 20% of maximum binding at a concentration of 10 µg/ml of unlabeled sample antibody. In some aspects, an antibody competes for binding if the sample antibody reduces the reference antibody's binding to NTB-A to levels less than 10% of maximum binding at a concentration of 10 µg/ml of unlabeled sample antibody. In some aspects, an antibody competes for binding if the sample antibody reduces the reference antibody's binding to NTB-A to levels less than 5% of maximum binding at a concentration of 10 µg/ml of unlabeled sample antibody. In some aspects, an antibody competes for binding if the sample antibody reduces the reference antibody's binding to NTB-A to levels less than 2% or less than 1% of maximum binding at a concentration of 10 µg/ml of unlabeled sample antibody. As can be seen from FIG. 2, the murine 11A1 antibody competes for binding with itself and with the 26B7 antibody. It does not compete for binding with the NT-7 antibody.

In some embodiments, an anti-NTBA antibody includes a heavy chain variable domain and/or light chain variable domain that is substantially identical to the heavy and/or light chain variable domain(s) of an antibody listed in Table 1.

Accordingly, in certain embodiments, an anti-NTB-A antibody has (a) a heavy chain variable domain that is at least 80%, at least 85%, at least 90%, at least 95%, at least 96%, at least 97%, at least 98%, at least 99%, or at least 99.5% identical to the amino acid sequence of a VH domain listed in Table 1 and/or (b) a light chain variable domain that is at least 80%, at least 85%, at least 90%, at least 95%, at least 96%, at least 97%, at least 98%, at least 99%, or at least 99.5% identical to the amino acid sequence of a VL domain listed in Table 1. In particular variations, the anti-NTB-A antibody includes (a) a heavy chain variable domain having the amino acid sequence of a VH domain listed in Table 1 and/or (b) a light chain variable domain having the amino acid sequence of a VL domain listed in Table 1. In some embodiments where an antibody comprises both a heavy chain variable domain and a light chain variable domain, the heavy and light chain variable domains correspond to the same reference antibody from Table 1. For example, in more specific variations, an anti-NTB-A antibody comprises light and heavy chain variable domains having respective VH and VL amino acid sequences selected from the following VH/VL sequence pairs: (I) residues 20-135 of SEQ ID NO:1 and residues 21-140 of SEQ ID NO:2; and (II) residues 20-137 of SEQ ID NO:3 and residues 21-128 of SEQ ID NO:4.

In some embodiments, an anti-NTB-A antibody of the present invention comprises one or more CDRs of an anti-NTB-A antibody listed in Table 1. The Kabat CDRs of the VH and VL domains from Table 1 are also set forth below in Table 2.

TABLE 2

CDR Sequences for Anti-NTB-A Antibody VH and VL Domains

| mAb | CDR | Amino Acid Sequence | SEQ ID NO: |
| --- | --- | --- | --- |
| 11A1 | CDR-H1 | dyyvh | 5 |
|  | CDR-H2 | kidpedgeikyapkfqg | 6 |
|  | CDR-H3 | ystyfdy | 7 |
|  | CDR-L1 | kaskkvtifgsisalh | 8 |
|  | CDR-L2 | ngakles | 9 |
|  | CDR-L3 | lqnkevpyt | 10 |

TABLE 2-continued

CDR Sequences for Anti-NTB-A Antibody VH and VL Domains

| mAb | CDR | Amino Acid Sequence | SEQ ID NO: |
| --- | --- | --- | --- |
| 26B7 | CDR-H1 | iywin | 11 |
|  | CDR-H2 | dihpgrgntnlnekfkt | 12 |
|  | CDR-H3 | ededwyfdv | 13 |
|  | CDR-L1 | rasqgisiwfn | 14 |
|  | CDR-L2 | ktsnlht | 15 |
|  | CDR-L3 | lqsqsypyt | 16 |

For example, in certain variations, the antibody comprises a heavy chain CDR (at least one of the CDR-H1, CDR-H2, and CDR-H3 regions) and/or a corresponding light chain CDR (at least one of the CDR-L1, CDR-L2, and CDR-L3 regions) of an antibody listed in Table 1. In typical embodiments, the anti-NTB-A antibody has two or three heavy chain CDRs and/or two or three light chain CDRs of an antibody listed in Table 1. In some variations, where an anti-NTB-A antibody has at least one heavy chain CDR of an antibody listed in Table 1, the antibody further comprises at least one corresponding light chain CDR.

In particular variations, an anti-NTB-A antibody includes a heavy and/or light chain variable domain, the heavy or light chain variable domain having (a) a set of three CDRs corresponding to the heavy or light chain CDRs as shown for an antibody listed in Table 1, and (b) a set of four framework regions. For example, an anti-NTB-A antibody can include a heavy and/or light chain variable domain, where the heavy or light chain variable domain has (a) a set of three CDRs, in which the set of CDRs are from an antibody listed in Table 1, and (b) a set of four framework regions, in which the set of framework regions are identical to or different (e.g., from a human framework region) from the set of framework regions of the same antibody listed in Table 1.

In certain variations, an anti-NTB-A antibody includes both (I) a heavy chain variable domain having (a) a set of three CDRs corresponding to the heavy chain CDRs as shown for an antibody listed in Table 1, and (b) a set of four framework regions; and (II) a light chain variable domain having (a) a set of three CDRs corresponding to the light chain CDRs as shown for an antibody listed in Table 1, and (b) a set of four framework regions. In typical embodiments, both the heavy chain and light chain CDRs are from the same antibody listed in Table 1.

In some embodiments, an anti-NTB-A antibody in accordance with the present invention includes a heavy and/or light chain variable region comprising at least one CDR having zero, one, two, three, or four amino acid substitutions (preferably conservative substitutions) relative to a CDR of a VL or VH domain listed in Table 1. In certain variations, for example, an anti-NTB-A antibody in accordance with the present invention comprises heavy chain CDRs CDR1-H1, CDR-H2, and CDR-H3, wherein at least one of CDR-H1, CDR2-H2, and CDR-H3 comprises zero, one, two, three, or four amino acid substitutions (preferably conservative substitutions) relative to a VH domain in Table 1. In other variations, an anti-NTB-A antibody in accordance with the present invention comprises light chain CDRs CDR1-L1, CDR2-L2, and CDR3-L3, wherein at least one of CDR1-L1, CDR2-L2, and CDR3-L3 comprises zero, one, two, three, or four amino acid substitutions (preferably conservative substitutions) relative to a VL domain listed in Table 1. In certain embodiments, an anti-NTB-A antibody comprises both sets of heavy chain and light chain CDRs as above.

Particularly suitable anti-NTB-A antibodies comprise a light chain variable domain comprising CDRs CDR1-L1, CDR2-L2, and CDR3-L3 and a heavy chain variable domain comprising CDRs CDR1-H1, CDR2-H2, and CDR3-H3, wherein said set of heavy and light chain CDRs has six or fewer, typically five or fewer, more typically four or fewer, and most typically 3 or fewer amino acid substitutions (preferably conservative substitutions) relative to CDRs from a VH domain and a VL domain listed in Table 1; in some such variations, the six or fewer amino acid substitutions are relative to CDRs from a VH domain and a VL domain of the same antibody listed in Table 1.

In certain embodiments, an anti-NTB-A antibody of the present invention comprises a humanized VH domain and/or a humanized VL domain respectively derived from a VH and/or VL domain listed in Table 1. In particular variations, the anti-NTB-A antibody comprises both a humanized VH domain and a humanized VL domain respectively derived from a VH domain and a VL domain listed in Table 1. Typically, the humanized VH and VL domains are derived from the same antibody listed in Table 1.

A humanized antibody is a genetically engineered antibody in which CDRs from a non-human "donor" antibody are grafted into human "acceptor" antibody sequences (see, e.g., Queen, U.S. Pat. Nos. 5,530,101 and 5,585,089; Winter, U.S. Pat. No. 5,225,539; Carter, U.S. Pat. No. 6,407,213; Adair, U.S. Pat. No. 5,859,205; and Foote, U.S. Pat. No. 6,881,557). The acceptor antibody sequences can be, for example, a mature human antibody sequence, a composite of such sequences, a consensus sequence of human antibody sequences, or a germline region sequence. Thus, a humanized antibody is an antibody having some or all CDRs entirely or substantially from a donor antibody and variable region framework sequences and constant regions, if present, entirely or substantially from human antibody sequences Similarly, a humanized VH domain has at least one, two, and usually all three CDRs entirely or substantially from a donor antibody VH domain, and variable region framework sequences entirely or substantially from a human antibody VH domain; such a humanized VH domain may be linked, typically amino-terminal to, an immunoglobulin heavy chain constant region entirely or substantially from a human heavy chain constant region sequence Similarly, a humanized VL domain has at least one, two, and usually all three CDRs entirely or substantially from a donor antibody VL domain, and variable region framework sequences entirely or substantially from a human antibody VL domain; such a humanized VL domain may be linked, typically amino-terminal to, an immunoglobulin light chain constant region entirely or substantially from a human light chain constant region sequence. Typically, a humanized antibody comprises both a humanized VH domain and a humanized VL domain. Generally, but not always, humanized antibodies will retain some non-human residues within the human variable domain framework regions to enhance proper binding characteristics (e.g., mutations in the frameworks may be required to preserve binding affinity when an antibody is humanized).

Although humanized antibodies often incorporate all six CDRs (preferably as defined by Kabat) from a non-human antibody, they can also be made with less than all CDRs (e.g., at least 3, 4, or 5) CDRs from a non-human antibody (e.g., Pascalis et al., *J. Immunol.* 169:3076, 2002; Vajdos et al., *J. Mol. Biol.,* 320: 415-428, 2002; Iwahashi et al., *Mol. Immunol.* 36:1079-1091, 1999; Tamura et al., *J. Immunol.,* 164:1432-1441, 2000). In some aspects, the humanized antibodies will incorporate all six CDRs but will have zero, one, two, or three conservative substitutions in one or more of the CDRs.

Certain amino acids from the human variable region framework residues can be selected for substitution based on their possible influence on CDR conformation and/or binding to antigen. Investigation of such possible influences is by modeling, examination of the characteristics of the amino acids at particular locations, or empirical observation of the effects of substitution or mutagenesis of particular amino acids.

For example, when an amino acid differs between a murine variable region framework residue and a selected human variable region framework residue, the human framework amino acid can be substituted by the equivalent framework amino acid from the mouse antibody when it is reasonably expected that the amino acid:

(1) noncovalently binds antigen directly,
(2) is adjacent to a CDR region,
(3) otherwise interacts with a CDR region (e.g., is within about 6 Å of a CDR region); or
(4) mediates interaction between the heavy and light chains.

Another possible variation is to substitute certain residues in the CDRs of the mouse antibody with corresponding residues from human CDR sequences, typically from the CDRs of the human acceptor sequences used in designing the exemplified humanized antibodies. In some antibodies only part of the CDRs, namely the subset of CDR residues required for binding, termed the SDRs, are needed to retain binding in a humanized antibody. CDR residues not contacting antigen and not in the SDRs can be identified based on previous studies (for example, residues H60-H65 in CDR H2 are often not required), from regions of Kabat CDRs lying outside Chothia hypervariable loops (Chothia, *J. Mol. Biol.* 196:901, 1987), by molecular modeling, and/or empirically, or as described in Gonzales et al., *Mol. Immunol.* 41: 863, 2004. In such humanized antibodies at positions in which one or more donor CDR residues is absent or in which an entire donor CDR is omitted, the amino acid occupying the position can be an amino acid occupying the corresponding position (by Kabat numbering) in the acceptor antibody sequence. The number of such substitutions of acceptor for donor amino acids in the CDRs to include reflects a balance of competing considerations. Such substitutions are potentially advantageous in decreasing the number of mouse amino acids in a humanized antibody and consequently decreasing potential immunogenicity. However, substitutions can also cause changes of affinity, and significant reductions in affinity are preferably avoided. In a further variation, one or more residues in a CDR of a humanized anti-NTB-A antibody (which would otherwise be the same as the CDR of an antibody listed in Table 1) can be replaced by corresponding residues from a CDR from a different antibody listed in Table 1. Positions for substitution within CDRs and amino acids to substitute can also be selected empirically.

Although not preferred, other amino acid substitutions can be made, for example, in framework residues not in contact with the CDRs, or even some potential CDR-contact residues or amino acids within the CDRs. Often the replacements made in the variant humanized sequences are conservative with respect to the replaced amino acids. Preferably, such replacements, whether or not conservative, have no substantial effect on the binding affinity or potency of the humanized antibody, that is, its ability to bind human NTB-A or inhibit growth of cancer cells.

Preferred anti-NTB-A antibodies or conjugated forms thereof (e.g., antibody-drug conjugates) inhibit cancer (e.g., growth of cells, metastasis and/or lethality to the organisms) as shown on cancerous cells propagating in culture, in an animal model, or in a clinical trial. Animal models can be formed by implanting NTB-A-expressing human tumor cell lines into appropriate immunodeficient rodent strains, e.g., athymic nude mice or SCID mice. These tumor cell lines can be established in immunodeficient rodent hosts either as solid tumor by subcutaneous injections or as disseminated tumors by intravenous injections. Once established within a host, these tumor models can be applied to evaluate the therapeutic efficacies of the anti-NTB-A antibodies or conjugated forms thereof.

In certain variations, an anti-NTBA antibody of the present invention comprises a VH and/or VL domain linked to at least a portion of an immunoglobulin constant region (e.g., a human immunoglobulin constant region). For example, in some embodiments, the anti-NTB-A antibody comprises first and second polypeptide chains, where the first polypeptide chain comprises a VH domain as described herein linked to at least a portion of an immunoglobulin heavy chain constant region and the second polypeptide chain comprises a VL domain as described herein linked to at least a portion of an immunoglobulin light chain constant region. Typically, the VH or VL domain is linked aminoterminal to an immunoglobulin constant region or portion thereof. In particular variations of an antibody comprising first and second polypeptide chains, the first and second polypeptide chains have a domain structure corresponding to the heavy and light chains of an intact native antibody, e.g., a first polypeptide (heavy) chain having the amino-terminal to carboxyl-terminal domain structure of VH-CH1-hinge-CH2-CH3 and a second polypeptide (light) chain having the amino-terminal to carboxyl-terminal domain structure of VL-CL.

In other embodiments, the anti-NTB-A antibody is a single-chain antibody comprising a VH domain, a VL domain, and at least a portion of an immunoglobulin constant region (e.g., a heavy chain constant region lacking a CH1 domain) linked within a single polypeptide chain. For example, the VH and VL domains may be constructed as a single-chain Fv (scFv) in either a VH/VL or VL/VH (amino-terminal/carboxyl-terminal) orientation, with the scFv linked (typically amino-terminal) to a heavy chain constant region, such as, e.g., a constant region comprising the CH2 and CH3 domains but lacking the CH1 domain. The scFv is typically linked to the constant region via a linker such as, for example, a linker derived from an immunoglobulin hinge region.

The choice of constant region can depend, in part, whether antibody-dependent cell-mediated cytotoxicity, antibody dependent cellular phagocytosis and/or complement dependent cytotoxicity are desired. For example, human isotypes IgG1 and IgG3 have strong complement-dependent cytotoxicity, human isotype IgG2 weak complement-dependent cytotoxicity and human IgG4 lacks complement-dependent cytotoxicity. Human IgG1 and IgG3 also induce stronger cell mediated effector functions than human IgG2 and IgG4. Light chain constant regions can be lambda or kappa. Antibodies can be expressed, e.g., as tetramers containing two light and two heavy chains, as separate heavy chains, light chains, as Fab, Fab', F(ab')2, and Fv, or as single chain antibodies in which heavy and light chain variable domains are linked through a spacer. Additionally, the constant regions can be mutated, if desired. In some aspects, a mutant form of a natural human constant region will have reduced binding to an Fcγreceptor relative to the natural human constant region.

Human constant regions show allotypic variation and isoallotypic variation between different individuals, that is, the constant regions can differ in different individuals at one or more polymorphic positions. Isoallotypes differ from allotypes in that sera recognizing an isoallotype binds to a non-polymorphic region of a one or more other isotypes.

One or several amino acids at the amino or carboxy terminus of the light and/or heavy chain, such as the C-terminal lysine of the heavy chain, may be missing or derivatized in a proportion or all of the molecules. Substitutions can be made in the constant regions to reduce or increase effector function such as complement-mediated cytotoxicity or ADCC (see, e.g., Winter et al., U.S. Pat. No. 5,624,821; Tso et al., U.S. Pat. No. 5,834,597; and Lazar et al., Proc. Natl. Acad. Sci. USA 103:4005, 2006), or to prolong half-life in humans (see, e.g., Hinton et al., J. Biol. Chem. 279:6213, 2004).

Exemplary substitution include the amino acid substitution of the native amino acid to a cysteine residue is introduced at amino acid position 234, 235, 237, 239, 267, 298, 299, 326, 330, or 332, preferably an S239C mutation in a human IgG1 isotype (US 20100158909). In some aspects, the presence of an additional cysteine residue allows interchain disulfide bond formation. Such interchain disulfide bond formation can cause steric hindrance, thereby reducing the affinity of the Fc region-FcγR binding interaction. The cysteine residue(s) introduced in or in proximity to the Fc region of an IgG constant region can also serve as sites for conjugation to therapeutic agents (i.e., coupling cytotoxic drugs using thiol specific reagents such as maleimide derivatives of drugs. The presence of a therapeutic agent causes steric hindrance, thereby further reducing the affinity of the Fc region-FcγR binding interaction. Other substitutions at any of positions 234, 235, 236 and/or 237 reduce affinity for Fcγ receptors, particularly FcγRI receptor (see, e.g., U.S. Pat. Nos. 6,624,821, 5,624,821.)

The in vivo half-life of an antibody can also impact on its effector functions. The half-life of an antibody can be increased or decreased to modify its therapeutic activities. FcRn is a receptor that is structurally similar to MHC Class I antigen that non-covalently associates with β2-microglobulin. FcRn regulates the catabolism of IgGs and their transcytosis across tissues (Ghetie and Ward, Annu. Rev. Immunol. 18:739-766, 2000; Ghetie and Ward, Immunol. Res. 25:97-113, 2002). The IgG-FcRn interaction takes place at pH 6.0 (pH of intracellular vesicles) but not at pH 7.4 (pH of blood); this interaction enables IgGs to be recycled back to the circulation (Ghetie and Ward, 2000, supra; Ghetie and Ward, 2002, supra). The region on human IgG1 involved in FcRn binding has been mapped (Shields et al., J. Biol. Chem. 276:6591-604, 2001). Alanine substitutions at positions Pro238, Thr256, Thr307, Gln311, Asp312, Glu380, Glu382, or Asn434 of human IgG1 enhance FcRn binding (Shields et al., supra). IgG1 molecules harboring these substitutions have longer serum half-lives. Consequently, these modified IgG1 molecules may be able to carry out their effector functions, and hence exert their therapeutic efficacies, over a longer period of time compared to unmodified IgG1. Other exemplary substitutions for increasing binding to FcRn include a Gln at position 250 and/or a Leu at position 428. EU numbering is used for all position in the constant region.

Oligosaccharides covalently attached to the conserved Asn297 are involved in the ability of the Fc region of an IgG to bind FcγR (Lund et al., *J. Immunol.* 157:4963-69, 1996; Wright and Morrison, *Trends Biotechnol.* 15:26-31, 1997). Engineering of this glycoform on IgG can significantly improve IgG-mediated ADCC. Addition of bisecting N-acetylglucosamine modifications (Umana et al., *Nat. Biotechnol.* 17:176-180, 1999; Davies et al., *Biotech. Bioeng.* 74:288-94, 2001) to this glycoform or removal of fucose (Shields et al., *J. Biol. Chem.* 277:26733-40, 2002; Shinkawa et al., *J. Biol. Chem.* 278:6591-604, 2003; Niwa et al., *Cancer Res.* 64:2127-33, 2004) from this glycoform are two examples of IgG Fc engineering that improves the binding between IgG Fc and FcγR, thereby enhancing Ig-mediated ADCC activity.

A systemic substitution of solvent-exposed amino acids of human IgG1 Fc region has generated IgG variants with altered FcγR binding affinities (Shields et al., *J. Biol. Chem.* 276:6591-604, 2001). When compared to parental IgG1, a subset of these variants involving substitutions at Thr256/Ser298, Ser298/Glu333, Ser298/Lys334, or Ser298/Glu333/Lys334 to Ala demonstrate increased in both binding affinity toward FcγR and ADCC activity (Shields et al., 2001, supra; Okazaki et al., *J. Mol. Biol.* 336:1239-49, 2004).

Complement fixation activity of antibodies (both C1q binding and CDC activity) can be improved by substitutions at Lys326 and G1u333 (Idusogie et al., *J. Immunol.* 166: 2571-2575, 2001). The same substitutions on a human IgG2 backbone can convert an antibody isotype that binds poorly to C1q and is severely deficient in complement activation activity to one that can both bind C1q and mediate CDC (Idusogie et al., supra). Several other methods have also been applied to improve complement fixation activity of antibodies. For example, the grafting of an 18-amino acid carboxyl-terminal tail piece of IgM to the carboxyl-termini of IgG greatly enhances their CDC activity. This is observed even with IgG4, which normally has no detectable CDC activity (Smith et al., *J. Immunol.* 154:2226-36, 1995). Also, substituting Ser444 located close to the carboxy-terminal of IgG1 heavy chain with Cys induced tail-to-tail dimerization of IgG1 with a 200-fold increase of CDC activity over monomeric IgG1 (Shopes et al., *J. Immunol.* 148:2918-22, 1992). In addition, a bispecific diabody construct with specificity for C1q also confers CDC activity (Kontermann et al., *Nat. Biotech.* 15:629-31, 1997).

Complement activity can be reduced by mutating at least one of the amino acid residues 318, 320, and 322 of the heavy chain to a residue having a different side chain, such as Ala. Other alkyl-substituted non-ionic residues, such as Gly, Ile, Leu, or Val, or such aromatic non-polar residues as Phe, Tyr, Trp and Pro in place of any one of the three residues also reduce or abolish C1q binding. Ser, Thr, Cys, and Met can be used at residues 320 and 322, but not 318, to reduce or abolish C1q binding activity. Replacement of the 318 (Glu) residue by a polar residue may modify but not abolish C1q binding activity. Replacing residue 297 (Asn) with Ala results in removal of lytic activity but only slightly reduces (about three fold weaker) affinity for C1q. This alteration destroys the glycosylation site and the presence of carbohydrate that is required for complement activation. Any other substitution at this site also destroys the glycosylation site. The following mutations and any combination thereof also reduce C1q binding: D270A, K322A, P329A, and P311S (see WO 06/036291).

Reference to a human constant region includes a constant region with any natural allotype or any permutation of residues occupying polymorphic positions in natural allotypes. Also, up to 1, 2, 5, or 10 mutations may be present relative to a natural human constant region, such as those indicated above to reduce Fcgamma receptor binding or increase binding to FcRn.

IV. Nucleic Acids and Methods of Production

The invention further provides nucleic acids encoding any of the VH and/or VL domains described above, including polypeptides comprising the VH and/or VL domains linked to additional polypeptide segments such, for example, polypeptide segments corresponding to an immunoglobulin constant region. Typically, the nucleic acids also encode a signal peptide fused amino-terminal to the mature polypeptide comprising the VH and/or VL domains. Coding sequences on nucleic acids can be in operable linkage with regulatory sequences to ensure expression of the coding sequences, such as a promoter, enhancer, ribosome binding site, transcription termination signal and the like. The nucleic acids can occur in isolated form or can be cloned into one or more vectors. The nucleic acids can be synthesized by for example, solid state synthesis or PCR of overlapping oligonucleotides. Nucleic acids encoding both a VH domain and a VL domain (e.g., in the context of antibodies comprising separate heavy and light chains) can be joined as one contiguous nucleic acid, e.g., within an expression vector, or can be separate, e.g., each cloned into its own expression vector.

Anti-NTB-A antibodies are typically produced by recombinant expression of one or more nucleic acids encoding one or more antibody chains. Recombinant polynucleotide constructs typically include an expression control sequence operably linked to the coding sequences of one or more polypeptide chains comprising VH and/or VL domains, including naturally-associated or heterologous promoter regions. Preferably, the expression control sequences are eukaryotic promoter systems in vectors capable of transforming or transfecting eukaryotic host cells. Once the vector has been incorporated into the appropriate host, the host is maintained under conditions suitable for high level expression of the nucleotide sequences, and the collection and purification of the cross-reacting antibodies.

In certain embodiments for the expression of antibodies comprising first and second polypeptide chains (e.g., heavy and light chains), the two polypeptide chains are co-expressed from separate vectors in the host cell for expression of the entire antibody molecule. In other embodiments for the expression of double-chained antibodies, the two polypeptide chains are co-expressed from separate expression units in the same vector in the host cell for expression of the entire antibody molecule.

Mammalian cells are a preferred host for expressing nucleotide segments encoding immunoglobulins or fragments thereof. See Winnacker, *From Genes to Clones*, (VCH Publishers, NY, 1987). A number of suitable host cell lines capable of secreting intact heterologous proteins have been developed in the art, and include CHO cell lines (e.g., DG44), various COS cell lines, HeLa cells, HEK293 cells, L cells, and non-antibody-producing myelomas including Sp2/0 and NS0. Preferably, the cells are non-human. Expression vectors for these cells can include expression control sequences, such as an origin of replication, a promoter, an enhancer (Queen et al., *Immunol. Rev.* 89:49, 1986), and necessary processing information sites, such as ribosome binding sites, RNA splice sites, polyadenylation sites, and transcriptional terminator sequences. Preferred expression control sequences are promoters derived from endogenous genes, cytomegalovirus, SV40, adenovirus, bovine papillomavirus, and the like. See Co et al., *J. Immunol.* 148:1149, 1992.

Once expressed, antibodies can be purified according to standard procedures of the art, including HPLC purification, column chromatography, gel electrophoresis and the like (see generally Scopes, *Protein Purification* (Springer-Verlag, NY, 1982)).

V. Antibody Drug Conjugates

Anti-NTB-A antibodies can be conjugated to cytotoxic or cytostatic moieties (including pharmaceutically compatible salts thereof) to form an antibody drug conjugate (ADC). Particularly suitable moieties for conjugation to antibodies are cytotoxic agents (e.g., chemotherapeutic agents), prodrug converting enzymes, radioactive isotopes or compounds, or toxins (these moieties being collectively referred to as a therapeutic agent). For example, an anti-NTB-A antibody can be conjugated to a cytotoxic agent such as a chemotherapeutic agent, or a toxin (e.g., a cytostatic or cytocidal agent such as, for example, abrin, ricin A, pseudomonas exotoxin, or diphtheria toxin). Examples of useful classes of cytotoxic agents include, for example, DNA minor groove binders, DNA alkylating agents, and tubulin inhibitors. Exemplary cytotoxic agents include, for example, auristatins, camptothecins, calicheamicins, duocarmycins, etoposides, maytansinoids (e.g., DM1, DM2, DM3, DM4), taxanes, benzodiazepines (e.g., pyrrolo[1,4]benzodiazepines, indolinobenzodiazepines, and oxazolidinobenzodiazepines) and vinca alkaloids.

An anti-NTB-A antibody can be conjugated to a pro-drug converting enzyme. The pro-drug converting enzyme can be recombinantly fused to the antibody or chemically conjugated thereto using known methods. Exemplary pro-drug converting enzymes are carboxypeptidase G2, beta-glucuronidase, penicillin-V-amidase, penicillin-G-amidase, β-lactamase, β-glucosidase, nitroreductase and carboxypeptidase A.

Techniques for conjugating therapeutic agents to proteins, and in particular to antibodies, are well-known. (See, e.g., Alley et al., *Current Opinion in Chemical Biology* 2010 14:1-9; Senter, *Cancer J.*, 2008, 14(3):154-169.) The therapeutic agent can be conjugated in a manner that reduces its activity unless it is cleaved off the antibody (e.g., by hydrolysis, by proteolytic degradation, or by a cleaving agent). In some aspects, the therapeutic agent is attached to the antibody with a cleavable linker that is sensitive to cleavage in the intracellular environment of the NTB-A-expressing cancer cell but is not substantially sensitive to the extracellular environment, such that the conjugate is cleaved from the antibody when it is internalized by the NTB-A-expressing cancer cell (e.g., in the endosomal or, for example by virtue of pH sensitivity or protease sensitivity, in the lysosomal environment or in the caveolear environment). In some aspects, the therapeutic agent can also be attached to the antibody with a non-cleavable linker Typically the ADC comprises a linker region between the therapeutic agent and the anti-NTB-A antibody. As noted supra, typically, the linker can be cleavable under intracellular conditions, such that cleavage of the linker releases the therapeutic agent from the antibody in the intracellular environment (e.g., within a lysosome or endosome or caveolea). The linker can be, e.g., a peptidyl linker that is cleaved by an intracellular peptidase or protease enzyme, including a lysosomal or endosomal protease. Cleaving agents can include cathepsins B and D and plasmin (see, e.g., Dubowchik and Walker, *Pharm. Therapeutics* 83:67-123, 1999). Most typical are peptidyl linkers that are cleavable by enzymes that are present in NTB-A-expressing cells. For example, a peptidyl linker that is cleavable by the thiol-dependent protease cathepsin-B, which is highly expressed in cancerous tissue, can be used (e.g., a linker comprising a Phe-Leu or a Val-Cit peptide).

The cleavable linker can be pH-sensitive, i.e., sensitive to hydrolysis at certain pH values. Typically, the pH-sensitive linker is hydrolyzable under acidic conditions. For example, an acid-labile linker that is hydrolyzable in the lysosome (e.g., a hydrazone, semicarbazone, thiosemicarbazone, cis-aconitic amide, orthoester, acetal, ketal, or the like) can be used. (See, e.g., U.S. Pat. Nos. 5,122,368; 5,824,805; 5,622,929; Dubowchik and Walker, *Pharm. Therapeutics* 83:67-123, 1999; Neville et al., *Biol. Chem.* 264:14653-14661, 1989.) Such linkers are relatively stable under neutral pH conditions, such as those in the blood, but are unstable at below pH 5.5 or 5.0, the approximate pH of the lysosome.

Other linkers are cleavable under reducing conditions (e.g., a disulfide linker) Disulfide linkers include those that can be formed using SATA (N-succinimidyl-S-acetylthioacetate), SPDP (N-succinimidyl-3-(2-pyridyldithio)propionate), SPDB (N-succinimidyl-3-(2-pyridyldithio)butyrate) and SMPT (N-succinimidyl-oxycarbonyl-alpha-methyl-alpha-(2-pyridyl-dithio)toluene), SPDB and SMPT. (See, e.g., Thorpe et al., *Cancer Res.* 47:5924-5931, 1987; Wawrzynczak et al., In *Immunoconjugates: Antibody Conjugates in Radioimagery and Therapy of Cancer* (C. W. Vogel ed., Oxford U. Press, 1987. See also U.S. Pat. No. 4,880,935.)

The linker can also be a malonate linker (Johnson et al., *Anticancer Res.* 15:1387-93, 1995), a maleimidobenzoyl linker (Lau et al., *Bioorg-Med-Chem.* 3:1299-1304, 1995), or a 3'-N-amide analog (Lau et al., *Bioorg-Med-Chem.* 3:1305-12, 1995).

The linker also can be a non-cleavable linker, such as an maleimido-alkylene- or maleimide-aryl linker that is directly attached to the therapeutic agent and released by proteolytic degradation of the antibody.

Typically, the linker is not substantially sensitive to the extracellular environment, meaning that no more than about 20%, typically no more than about 15%, more typically no more than about 10%, and even more typically no more than about 5%, no more than about 3%, or no more than about 1% of the linkers in a sample of the ADC is cleaved when the ADC is present in an extracellular environment (e.g., in plasma). Whether a linker is not substantially sensitive to the extracellular environment can be determined, for example, by incubating independently with plasma both (a) the ADC (the "ADC sample") and (b) an equal molar amount of unconjugated antibody or therapeutic agent (the "control sample") for a predetermined time period (e.g., 2, 4, 8, 16, or 24 hours) and then comparing the amount of unconjugated antibody or therapeutic agent present in the ADC sample with that present in control sample, as measured, for example, by high performance liquid chromatography.

The linker can also promote cellular internalization. The linker can promote cellular internalization when conjugated to the therapeutic agent (i.e., in the milieu of the linker-therapeutic agent moiety of the ADC or ADC derivate as described herein). Alternatively, the linker can promote cellular internalization when conjugated to both the therapeutic agent and the anti-NTB-A antibody (i.e., in the milieu of the ADC as described herein).

Exemplary antibody-drug conjugates include auristatin based antibody-drug conjugates meaning that the drug component is an auristatin drug. Auristatins bind tubulin, have been shown to interfere with microtubule dynamics and nuclear and cellular division, and have anticancer activity. Typically the auristatin based antibody-drug conjugate comprises a linker between the auristatin drug and the anti-NTB-A antibody. The linker can be, for example, a cleavable linker (e.g., a peptidyl linker) or a non-cleavable linker (e.g., linker released by degradation of the antibody). The auristatin can be auristatin E or a derivative thereof. The auristatin can be, for example, an ester formed between auristatin E and a keto acid. For example, auristatin E can be reacted with paraacetyl benzoic acid or benzoylvaleric acid to produce AEB and AEVB, respectively. Other typical auristatins include MMAF, and MMAE. The synthesis and structure of exemplary auristatins are described in U.S. Publication Nos. 7,659,241, 7,498,298, 2009-0111756, 2009-0018086, and 7,968, 687 each of which is incorporated herein by reference in its entirety and for all purposes.

Exemplary auristatin based antibody drug conjugates include vcMMAE, vcMMAF and mcMMAF antibody drug conjugates as shown below wherein Ab is an antibody as described herein and val-cit represents the valine-citrulline dipeptide:

antibody is attached to the drug-linker through a cysteine residue of the antibody. In some aspects, the cysteine residue is one that is engineered into the antibody. In other aspects, the cysteine residue is an interchain disulfide cysteine residue.

VI. Applications

In another aspect, the present invention provides methods of using an anti-NTBA-antibody as described herein to modulate a biological activity of an NTB-A-expressing cell, including, for example, natural killer (NK) cells, NK-like T-cells, T-cells, monocytes, dendritic cells, B-cells, and eosinophils. Such methods include, for example, methods of inhibiting an activity of an NTB-A-expressing cell (e.g., inhibiting cell proliferation). Such methods further include, e.g., methods for treatment of a disease or disorder associated with an NTB-A-expressing cell.

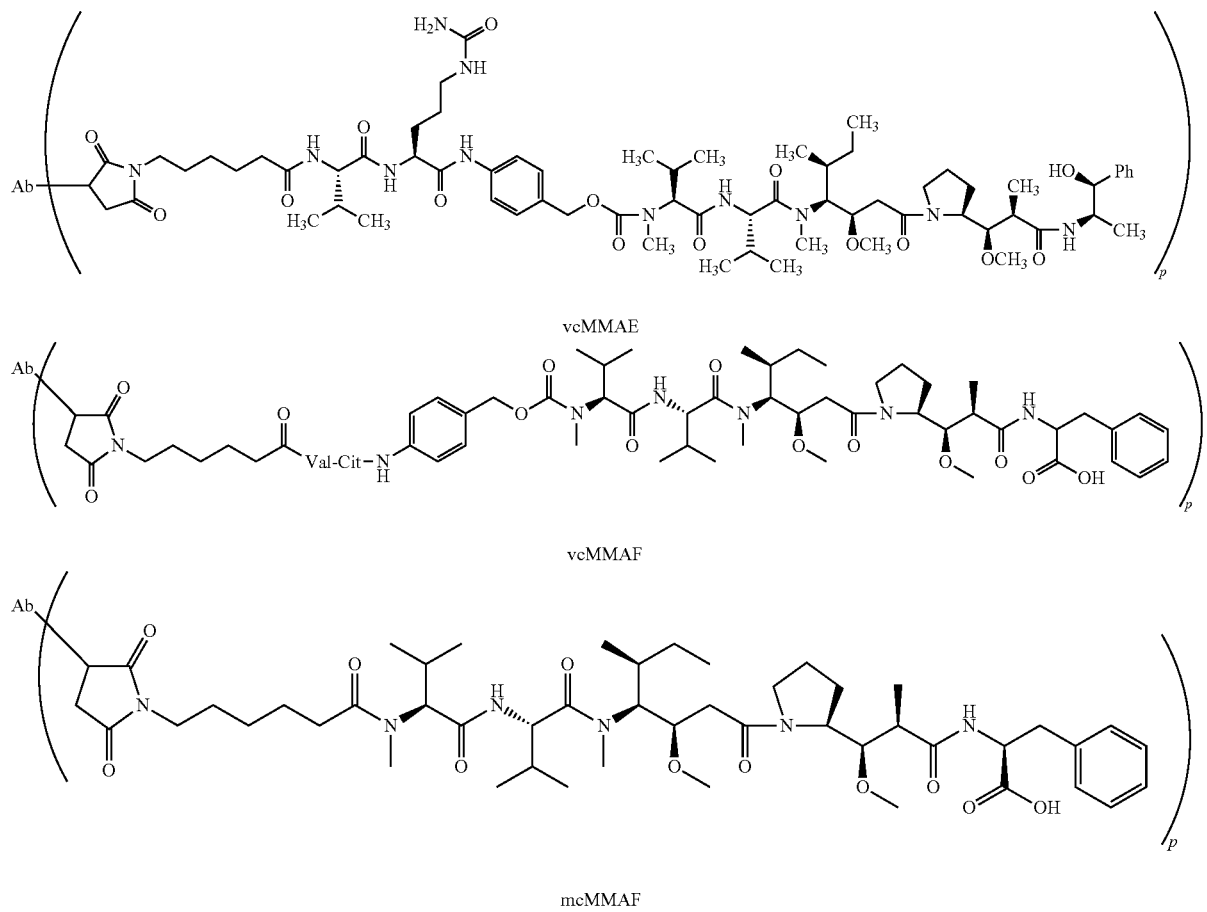

vcMMAE vcMMAF mcMMAF or a pharmaceutically acceptable salt thereof. The drug loading is represented by p, the number of drug-linker molecules per antibody. Depending on the context, p can represent the average number of drug-linker molecules per antibody, also referred to the average drug loading. P ranges from 1 to 20 and is preferably from 1 to 8. In some preferred embodiments, when p represents the average drug loading, p ranges from about 2 to about 5. In some embodiments, p is about 2, about 3, about 4, or about 5. The average number of drugs per antibody in a preparation may be characterized by conventional means such as mass spectroscopy, HIC, ELISA assay, and HPLC. In some aspects, the anti-NTBA For example, the anti-NTBA antibodies of the present invention, as naked antibodies or as antibody drug conjugates thereof, can be used to treat an NTB-A-expressing cancer. Some such cancers show detectable levels of NTB-A measured at either the protein (e.g., by immunoassay using one of the exemplified antibodies) or mRNA level. Some such cancers show elevated levels of NTB-A relative to noncancerous tissue of the same type, preferably from the same patient. An exemplary level of NTB-A on cancer cells amenable to treatment is 5000-150000 NTB-A molecules per cell, although higher or lower levels can be treated.

Optionally, a level of NTB-A in a cancer is measured before performing treatment.

Examples of cancers associated with NTB-A expression and amenable to treatment include hematological malignancies, including B-cell, T-cell, and NK-cell malignancies. In some embodiments, the cancer is a multiple myeloma, an acute myeloid leukemia (AML), a chronic lymphocytic leukemia (CLL), or a T-Cell or B-cell lymphoma such as, e.g., a non-Hodgkin's lymphoma (NHL). The treatment can be applied to patients having primary or metastatic tumors of these kinds. The treatment can also be applied to patients who are refractory to conventional treatments, or who have relapsed following a response to such treatments.

In a related aspect, the present invention provides a method of treating multiple myeloma using an antibody-drug conjugate (ADC) comprising an antibody that specifically binds to NTB-A. In certain variations of this aspect, an anti-NTB-A ADC for treating multiple myeloma comprises an anti-NTB-A antibody as described herein (e.g., a humanized antibody comprising VH and VL domains respectively derived from a VH domain having the amino acid sequence as shown in residues 20-135 of SEQ ID NO:1 and a VL domain having the amino acid sequence as shown in residues 21-140 of SEQ ID NO:2). In other aspects, an anti-NTB-A ADC for treating multiple myeloma comprises an antibody other than an antibody as described herein that specifically binds to an extracellular domain of NTB-A. A collection of anti-NTB-A antibodies are known in the art. Additional antibodies to anti-NTB-A can be made de novo, for example, by immunizing with NTB-A or one or more extracellular domains thereof. Such an immunogen can be obtained from a natural source, by peptide synthesis or by recombinant expression. Human antibodies against NTB-A can be provided by a variety of techniques known in the art.

The anti-NTBA antibodies of the present invention, as naked antibodies or as antibody drug conjugates thereof, can be used to treat diseases and disorders associated with B cells, e.g., those diseases characterized by excessive numbers of B cells, overactive B cells, or dysfunctional B cells. These diseases include inflammatory diseases and autoimmune disease. Exemplary diseases treatable by the present methods include rheumatoid arthritis, systemic lupus erythematosus, multiple sclerosis, inflammatory bowel disease, asthma, allergy, celiac disease, graft-versus-host disease, and transplant rejection.

The present invention encompasses methods of treating the disease and disorders described herein as a monotherapy or in combination therapy with, for example, standard of care for treatment of such diseases and/or disorders. Accordingly, methods for the treatment of cancer include administering to a patient in need thereof an effective amount of an antibody or antibody drug conjugate of the present invention in combination with an additional anti-cancer agent or other agent to alleviate symptoms of the cancer. Methods for the treatment of autoimmune disease include administering to a patient in need thereof an effective amount of an antibody or antibody drug conjugate of the present invention in combination with an additional therapeutic agent for the treatment of autoimmune disease. Methods for the treatment of inflammatory disease include administering to a patient in need thereof an effective amount of an antibody or antibody drug conjugate of the present invention in combination with an additional therapeutic agent for the treatment of inflammatory disease.

Anti-NTB-A antibodies, alone or as conjugates thereof, are administered in an effective regime meaning a dosage, route of administration and frequency of administration that delays the onset, reduces the severity, inhibits further deterioration, and/or ameliorates at least one sign or symptom of cancer. In some instances, therapeutic efficacy can be observed in an individual patient relative to historical controls or past experience in the same patient. In other instances, therapeutic efficacy can be demonstrated in a preclinical or clinical trial in a population of treated patients relative to a control population of untreated patients.

Exemplary dosages for an anti-NTB-A antibody are 0.1 mg/kg to 50 mg/kg of the patient's body weight, more typically 1 mg/kg to 30 mg/kg, 1 mg/kg to 20 mg/kg, 1 mg/kg to 15 mg/kg, 1 mg/kg to 12 mg/kg, or 1 mg/kg to 10 mg/kgl, or 2 mg/kg to 30 mg/kg, 2 mg/kg to 20 mg/kg, 2 mg/kg to 15 mg/kg, 2 mg/kg to 12 mg/kg, or 2 mg/kg to 10 mg/kg, or 3 mg/kg to 30 mg/kg, 3 mg/kg to 20 mg/kg, 3 mg/kg to 15 mg/kg, 3 mg/kg to 12 mg/kg, or 3 mg/kg to 10 mg/kg. Exemplary dosages for a monoclonal antibody or antibody drug conjugates thereof are 0.1 mg/kg to 7.5 mg/kg, 0.2 mg/kg to 7.5 mg/kg, 0.5 mg/kg to 7.5 mg/kg, 1 mg/kg to 7.5 mg/kg, or 2 mg/kg to 7.5 mg/kg or 3 mg/kg to 7.5 mg/kg of the subject's body weight, or 0.1-20, or 0.5-5 mg/kg body weight (e.g., 0.5, 1, 2, 3, 4, 5, 6, 7, 8, 9 or 10 mg/kg) or 10-1500 or 200-1500 mg as a fixed dosage. In some methods, the patient is administered a dose of at least 0.3 mg/kg, 0.5 mg/kg, 1 mg/kg 1.5 mg/kg, at least 2 mg/kg or at least 3 mg/kg, administered once every three weeks or greater. The dosage depends on the frequency of administration, condition of the patient and response to prior treatment, if any, whether the treatment is prophylactic or therapeutic and whether the disorder is acute or chronic, among other factors.

Administration is typically parenteral. Administration can also be localized directly into a tumor. Administration into the systemic circulation by intravenous or subcutaneous administration is preferred. Intravenous administration can be, for example, by infusion over a period such as 30-90 min or by a single bolus injection.

The frequency of administration depends on the half-life of the antibody or conjugate in the circulation, the condition of the patient and the route of administration among other factors. The frequency can be daily, weekly, monthly, quarterly, or at irregular intervals in response to changes in the patient's condition or progression of the cancer being treated. An exemplary frequency for intravenous administration is between twice a week and quarterly over a continuous course of treatment, although more or less frequent dosing is also possible. Other exemplary frequencies for intravenous administration are between weekly or three out of every four weeks over a continuous course of treatment, although more or less frequent dosing is also possible. For subcutaneous administration, an exemplary dosing frequency is daily to monthly, although more or less frequent dosing is also possible.

The number of dosages administered depends on the nature of the cancer (e.g., whether presenting acute or chronic symptoms) and the response of the disorder to the treatment. For acute disorders or acute exacerbations of a chronic disorder between 1 and 10 doses are often sufficient. Sometimes a single bolus dose, optionally in divided form, is sufficient for an acute disorder or acute exacerbation of a chronic disorder. Treatment can be repeated for recurrence of an acute disorder or acute exacerbation. For chronic disorders, an antibody can be administered at regular intervals, e.g., weekly, fortnightly, monthly, quarterly, every six months for at least 1, 5 or 10 years, or the life of the patient.

Pharmaceutical compositions for parenteral administration are preferably sterile and substantially isotonic and manufactured under GMP conditions. Pharmaceutical compositions can be provided in unit dosage form (i.e., the dosage for a single administration). Pharmaceutical compositions can be formulated using one or more physiologically acceptable carriers, diluents, excipients or auxiliaries. The formulation depends on the route of administration chosen. For injection, antibodies can be formulated in aqueous solutions, preferably in physiologically compatible buffers such as Hank's solution, Ringer's solution, or physiological saline or acetate buffer (to reduce discomfort at the site of injection). The solution can contain formulatory agents such as suspending, stabilizing and/or dispersing agents. Alternatively antibodies can be in lyophilized form for constitution with a suitable vehicle, e.g., sterile pyrogen-free water, before use. The concentration of antibody in a liquid formulation can be e.g., 1-100 mg/ml, such as 10 mg/ml.

Treatment with antibodies of the invention can be combined with chemotherapy, radiation, stem cell treatment, surgery other treatments effective against the disorder being treated. Useful classes of other agents that can be administered with an anti-NTB-A antibody include, for example, antibodies to other receptors expressed on cancerous cells, antitubulin agents (e.g., auristatins), DNA minor groove binders, DNA replication inhibitors, alkylating agents (e.g., platinum complexes such as cis-platin, mono(platinum), bis(platinum) and tri-nuclear platinum complexes and carboplatin), anthracyclines, antibiotics, antifolates, antimetabolites, chemotherapy sensitizers, duocarmycins, etoposides, fluorinated pyrimidines, ionophores, lexitropsins, nitrosoureas, platinols, pre-forming compounds, purine antimetabolites, puromycins, radiation sensitizers, steroids, taxanes, topoisomerase inhibitors, vinca alkaloids, and the like.

Treatment with the anti-NTB-A antibody, optionally in combination with any of the other agents or regimes described above alone or as an antibody drug conjugate, can increase the median progression-free survival or overall survival time of patients with an NTB-A-expressing cancer (e.g., multiple myeloma, AML, NHL), especially when relapsed or refractory, by at least 30% or 40% but preferably 50%, 60% to 70% or even 100% or longer, compared to the same treatment (e.g., chemotherapy) but without an anti-NTB-A antibody alone or as a conjugate. In addition or alternatively, treatment (e.g., standard chemotherapy) including the anti-NTB-A antibody alone or as a conjugate can increase the complete response rate, partial response rate, or objective response rate (complete+partial) of patients with an NTB-A-expressing cancer by at least 30% or 40% but preferably 50%, 60% to 70% or even 100% compared to the same treatment (e.g., chemotherapy) but without the anti-NTB-A antibody.

Typically, in a clinical trial (e.g., a phase II, phase II/III or phase III trial), the aforementioned increases in median progression-free survival and/or response rate of the patients treated with standard therapy plus the anti-NTB-A antibody, relative to the control group of patients receiving standard therapy alone (or plus placebo), are statistically significant, for example at the p=0.05 or 0.01 or even 0.001 level. The complete and partial response rates are determined by objective criteria commonly used in clinical trials for cancer, e.g., as listed or accepted by the National Cancer Institute and/or Food and Drug Administration.

In other applications, the anti-NTB-A antibodies of the present invention can be used for detecting NTB-A in the context of clinical diagnosis or treatment or in research. Expression of NTB-A on a cancer provides an indication that the cancer is amenable to treatment with the antibodies of the present invention. The antibodies can also be sold as research reagents for laboratory research in detecting cells bearing NTB-A and their response to various stimuli. In such uses, an anti-NTB-A antibody can be labeled with a fluorescent molecule, a spin-labeled molecule, an enzyme, or a radioisotope, and can be provided in the form of kit with all the necessary reagents to perform the assay for NTB-A. The antibodies can also be used to purify NTB-A, e.g., by affinity chromatography.

All patent filings, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise if different versions of a publication are published at different times, the version most recently published at the effective filing date of the application is meant unless otherwise indicated. Any feature, step, element, embodiment, or aspect of the invention can be used in combination with any other unless specifically indicated otherwise. Although the present invention has been described in some detail by way of illustration and example for purposes of clarity and understanding, it will be apparent that certain changes and modifications may be practiced within the scope of the appended claims.

EXAMPLES

Example 1

Expression of NTB-A on Multiple Myeloma Cell Lines

Amo-1, JJN-3, Karpas-620, KMS-12-BM, MOLP-8, OPM-2 (DSMZ; RPMI 1640 +20% FBS), L-363 (DSMZ; RPMI 1640 +15% FBS), LP-1, SK-MM-2 (DSMZ; RPMI 1640 +10% FBS), EJM (DSMZ; EMEM +20% FBS), MM.1R, MM.1S, NCI-H929, RPMI-8226 (ATCC; RPMI 1640 +10% FBS), and U-266 (ATCC; RPMI 1640 +15% FBS) cell lines were cultured at 37° C., 5% CO2. 500,000 cells were stained in FACs buffer (PBS +3% FBS +0.02% sodium azide) for 45 minutes on ice with anti-NTB-A antibodies NT-7 and 11A1. A PE-conjugated secondary antibody was used for detection. Stained cells were analyzed using a FACSCalibur flow cytometer (Becton Dickinson).

NTB-A was shown to be expressed on five of fifteen multiple myeloma cell lines, Karpas-620, EJM, MM.1R, MM.1S and U-266.

Example 2

Expression of NTB-A on Multiple Myeloma Patient Samples

Frozen human multiple myeloma patient bone marrow aspirate samples (5-10 million cells) were purchased from BioServe (Beltsville, Md.), AllCells (Emeryville, Calif.), Conversant Healthcare Systems (Huntsville, Ala.), and ProteoGenex (Culver City, Calif.). MM patient bone marrow cells were thawed at 37° C., transferred into prewarmed RPMI 1640 media, and treated with DNase 1 (0.05 mg/mL) for 10 minutes at room temperature to minimize cell aggregation. The cells were then centrifuged (1,400 rpm; 5 minutes), resuspended into RPMI 1640 +10% FBS), and cell number/viability measured by trypan blue exclussion. Next, the patient cells were centrifuged, resuspended into FACs buffer (PBS +3% FBS, +0.02% sodium azide) on ice, filtered through a 100 μm cell strainer to remove any debris, and 100 μL cell suspension aliquoted into the wells of a V-bottom 96-well plate for staining (1.2×105-1.0×106 viable cells/well). The patient bone marrow aspirate cells were triple stained with anti-hCD38-FITC, anti-hCD45-APC and PE-conjugated anti-NTB-A (clone: NT-7) or isotype control IgG (30 minutes on ice). Stained cells were washed twice in FACs buffer and analyzed by flow cytometry using the FACsCalibur flow cytometer. Cell surface expression of NTB-A was quantitated for the multiple myeloma cell CD38+/CD45− gated subpopulation. Expression of CD138 (clone:1D4) positive control multiple myeloma antigen was also measured.

NTB-A was shown to be expressed on the surface of 13 out of 15 patient samples. See Table 3 below:

TABLE 3

Results Summary for NTB-A Expression on Human Multiple Myeloma Patient Plasma Cells

| Multiple Myeloma Patient | Treatment History | NTB-A Expression (clone: NT-7) | CD138 Expression (clone: 1D4) |
|---|---|---|---|
| 1 | Stage III; relapsed | 2.37 | 1.51 |
| 2 | Newly diagnosed | 15.4 | 7.99 |
| 3 | Newly diagnosed | 79.8 | 143 |
| 4 | VAD chemotherapy; Autologous transplant | 25.0 | 745 |
| 5 | VAD chemotherapy | 14.0 | 12.8 |
| 6 | Bone marrow transplant; Bortezomib | 1.16 | 1.65 |
| 7 | Newly diagnosed | 18.2 | 1.45 |
| 8 | Newly diagnosed | 87.3 | 46.6 |
| 9 | Newly diagnosed | 85.7 | 17.3 |
| 10 | Chemotherapy; Autologous transplant | 1.22 | 106 |
| 11 | Melphalan, Lenalidomide | 5.09 | 2.20 |
| 12 | Lenalidomide, Cytoxan, Thalidomide | 7.56 | 3.25 |
| 13 | Bortezomib | 17.3 | 4.55 |
| 14 | VAD chemotherapy; Lenalidomide, Bortezomib | 17.8 | 74.33 |
| 15 | Newly Diagnosed | 12.7 | 11.45 |

Fold increase of antigen expression (mean fluorescence intensity) over isotype control antibody Example 3

Antibody Selection

Lymphocytes harvested from spleen and lymph nodes of NTB-A antibody producing mice were fused to myeloma cells. Fused cells were recovered overnight in hybridoma growth media. Following recovery, cells were spun down and then plated in semi-solid media. Hybridomas were incubated and IgG producing hybridoma clones were picked. Hybridoma culture supernatants were screened and 313 out of 478 hybridoma clones were found to specifically bind to NTB-A extracellular domain by measuring fluorescent signal on the surface of NTB-A positive cells. Specific binding of fluorescent labelled ADCs to extracellular domain NTB-A was confirmed by flow cytometry (BD Biosciences FACSCalibur) using a panel of NTB-A expressing multiple myeloma cells at 2.0 ocg/ml concentration. The 313 hybridomas that bound to NTB-A were expanded for direct conjugation with vc-MMAE using the methods described in International Application No. WO 2011/109308. The directly conjugated antibody panel was tested in binding and cytotoxicity assays. The 313 NTBA-A binding ADCs were screened for cytotoxicity with multiple myeloma cell lines. Cytoxicity studies were done by plating 15,000 multiple myeloma cells per well in the appropriate growth media. For cell-based binding assays, anti-NTB-A vcMMAE 4-loaded antibody drug conjugates were tested at 12.5, 50.0, and 200 ng/mL final concentration on cells and incubated for 96 hours total at 37° C. Cell viability was measured using the Cell Titer Glo (Promega) luminescence assay and the potency of ADCs was assessed based on the percent viability relative to untreated control cells. $IC_{50}$ values were generated from dose curves produced using Prism software (GraphPad). The cytotoxicity cut-off was set at an $IC_{50}$ less than or equal to 50 ng/ml. The 69 most potent anti-NTBA monoclonal antibodies as ADCs were moved forward. Only 6 of the 69 most potent ADCs demonstrated an $IC_{50}$ value less than 12.5 ng/ml. Saturation binding curves and Kd values were determined by flow cytometry for a small panel of the highly cytotoxic anti-NTB-A ADCs. Anti-NTB-A ADCs with the 11A1 and 26B7 antibodies were determined to be the most cytotoxic.

Example 4

Anti-NTB-A Internalization Assay

The murine 11A1 antibody mcMMAF conjugate was evaluated for its ability to internalize in the NTB-A+ cell line U-266 (FIG. 1).

U-266 antigen-positive cells were incubated with 5 μg/mL anti-human NTB-A antibody drug conjugate, 11A1-mcMMAF (the antimitotic agent MMAF conjugated via a maleimidocaproyl linker (mc) to a stoichiometry of 4 drugs per antibody via cysteine linkages) for 30 minutes on a shaker at 4° C. Cells were washed three times with RPMI 1640 media +10% fetal bovine serum and then plated out at 5×105 cells/100 μL per well into two identical 96-well U-bottom plates (BioSciences, San Jose, Calif.). One plate was placed at 37° C. and the other at 4° C. One sample was immediately washed and stained for time zero. Cells were collected from both plates at 0.5, 1, 2, 8, and 24 hour time points, washed two times with cold wash buffer (PBS+2.5% fetal bovine serum), and stained with 10 μg/mL goat-anti-mouse IgG-PE (Jackson ImmunoResearch, West Grove, Pa.) for 30 minutes, on ice and protected from light. Cells were again washed twice with wash buffer and fixed with 500 μL of PBS+1% paraformaldehyde. Once all samples were collected and stained, they were analyzed on the FACs Calibur flow cytometer (BD BioSciences, San Jose, Calif.), and data was expressed as a percentage of time zero MFI.

Example 5

ADC Cytotoxicity Assays

Antibody-drug conjugates (ADCs) were prepared for the murine anti-NTB-A monoclonal antibodies 11A1 and 26B7. The antimitotic agent monomethyl auristatin E (MMAE) was conjugated to anti-NTB-A mAbs via a cathepsin-cleavable valine-citrulline (vc) linker and monomethyl auristatin F (MMAF) was conjugated via a maleimidocaproyl (mc) linker to a stoichiometry of 4 drugs per antibody via cysteine linkage as described in U.S. Pat. Nos. 7,659,241 and 7,498,298. Anti-NTB-A-vc-MMAE(4) and –mc-MMAF(4) ADCs were serially diluted 3-fold in media to produce a 10 point dose curve (1,000 ng/mL-0.05081 ng/mL) and applied to multiple myeloma cells cultured in 96-well assay plates. Karpas-620, EJM, MM.1R, MM.1S, U-266 (NTB-A+), and L363 (NTB-A−) multiple myeloma cell lines were treated with anti-NTB-A ADCs in quadruplicate and incubated for 96 hours at 37° C., 5% CO2. Cells were assayed for viability using the Cell Titer Glo luminescent cytotoxicity assay (Promega), and data collected using an EnVision plate reader (Perkin Elmer). Dose effect curves and IC50 values were calculated using GraphPad Prism software

TABLE 4

Results Summary for ADC Cytotoxicity Assay against multiple myeloma cell lines

| Ab | Drug | Karpas-620 | EJM | MM.1S | U-266 | MM.1R | Iso-type |
|---|---|---|---|---|---|---|---|
| 11A1 | vcMMAE | 3.77 | 12.5 | 48.9 | 2.37 | 13.6 | mIgG1 |
| 11A1 | mcMMAF | 0.648 | 2.48 | 3.10 | 0.877 | 2.52 | mIgG1 |
| 26B7 | vcMMAE | 431 | 52.5 | >1000 | 6.04 | 78.9 | mIgG1 |
| 26B7 | mcMMAF | 2.61 | 6.07 | 3.99 | 1.72 | 5.86 | mIgG1 |

TABLE 5

Result Summary for ADC Cytotoxicity Assay against AML and NHL cell lines

| Ab | Drug | CA46 (NHL) | Ramos (NHL) | HNT-34 (AML) | HEL92.1.7 (AML) | KG-1 (AML) | Isotype |
|---|---|---|---|---|---|---|---|
| 11A1 | vcMMAE | 8.91 | 5.77 | 1.58 | >1000 | 14.0 | mIgG1 |
| 11A1 | mcMMAF | 2.61 | 1.76 | 0.861 | >1000 | 2.09 | mIgG1 |
| 26B7 | vcMMAE | 13.8 | 6.83 | 3.26 | >1000 | 178.2 | mIgG1 |
| 26B7 | mcMMAF | 4.91 | 3.19 | 1.13 | >1000 | 2.45 | mIgG1 |

Example 6

Competitive Binding Assay

The assay described in this example details the method used to evaluate the ability of a sample antibody to compete for binding with the 11A1 murine antibody. For this particular study, the ability of the 26B7 antibody and the NT-7 antibody (clone: NT-7 (Biolegend #317208) to compete with the 11A1 antibody was evaluated. Also evaluated was the ability of the 11A1 antibody to compete with itself. The assay utilizes a "reference antibody" comprising the murine 11A1 IgG1 antibody (i.e., VH and VL domains in the bivalent structure of a native (natural) antibody, i.e., a tetramer consisting of two identical pairs of immunoglobulin chains, each pair having one light chain and one heavy chain.)

Exponentially growing NTB-A positive cells expressing about 24,500 NTB-A surface molecules per cell (e.g., Ramos cells) was collected and washed in isotonic phosphate buffered saline (PBS) and stored on ice. The NTB-A positive cells were aliquoted into wells of a 96-well v-bottom plate on ice, $2\times10^5$ cells per well in 100 μL volume per well.

A 2× concentration of the reference antibody conjugated to a fluorescent label (e.g., AF647) was prepared in PBS/FBS (PBS containing 2% fetal bovine serum (FBS)/0.02% sodium azide), with the 1× concentration being equal to 0.0188 μg/mL (the Kd value concentration of 11A1 mAb). This PBS/FBS/Labeled-Ab solution was then aliquoted into wells of a 96-well dilution plate (200 μL/well). Row A of wells was left for the initial 2× mix of unlabeled sample antibody in the PBS/FBS/Labeled-Ab solution (see item (4) below); sufficient wells were also left for controls.

A 2× concentration of an unlabeled sample antibody (to be evaluated for competitive binding) was prepared in the PBS/FBS AF Labeled-Ab solution (20 μg/mL of sample antibody; therefore, the 1× concentration equal to 10 μg/mL). The 2× concentration of unlabeled sample antibody was then aliquoted to wells in the first column of the 96-well dilution plate. Samples were then serially diluted in a five-fold dilution series (50 μL from the initial sample dilution is added to the 200 μL of the PBS/FBS/Labeled-Ab solution in the next row, repeating from row to row of the plate).

Sufficient wells (e.g., wells A1 through A6) were left for flow cytometry set up and unstained wells, with PBS/FBS only added (no labeled reference antibody). These wells were used as the unstained controls (0% staining). Sufficient wells (e.g., wells A7 though A12) were also left to serve as the 100% staining and receive the PBS/FBS/Labeled-Ab solution without unlabeled sample antibody.

100 μL of diluted samples from the dilution plate were then transferred in duplicate to corresponding wells of cells (100 μL) in the v-bottom plate to yield 1× concentrations. These samples were then incubated for one hour on ice protected from light.

Cells were then washed twice with PBS/FBS. For example, the plate was spun down at 1000 rpm for 5 minutes and the supernatant discarded, plates vortexed to disperse cells, and wash buffer (PBS/FBS) added (about 200 μL/well/wash); after the last spin, the plate was inverted and blotted gently.

Following the wash, cell pellets were resuspended in 250 μL of PBS/FBS and the cells were kept at 2-8° C., protected from light, until analyzed on a flow cytometer (e.g., an LSRII flow cytometer, BD BioSciences, San Jose, Calif.).

Once on the flow cytometer, the cell population of interest was isolated by gating on forward scatter and side scatter populations (FSC/SSC) to yield population plots, and the fluorescence signal for the fluorescent label was acquired.

The flow cytometry data was then analyzed using a sigmoidal dose-response analysis (variable slope). The IC50 of the unlabeled antibody was determined from the fitted curve (i.e., the concentration of the unlabeled sample antibody at which the labeled reference antibody exhibits 50% of maximum binding).

The 11A1 antibody competed with itself and with antibody 26B7 but not with antibody NT-7. Only those antibodies that reduce 11A1 binding to less than 45% of maximum binding at a concentration of 10 ug/ml of unlabeled sample antibody (preferably less than 20% or even less than 10%) are deemed to compete with 11A1 for binding to NTB-A.

The 11A1 and 26B7 antibodies were also tested for competition with the 480.12 antibody using FACS-based competition assays as described in U.S. Pat. No. 7,874,067. The 11A1 and 26B7 antibodies did not compete for binding with the 480.12 antibody in such assays (data not shown).

Example 7 mAb Affinity Measurements and Binding Specificity

Dose titrations of the murine anti-human NTB-A antibodies conjugated to Alexa Fluor 647 (11A1 and 26B7) were used to generate a saturation binding curve. Antigen positive Ramos cells were plated at $1 \times 10^5$ cells per well in a 96 well V-bottom plate (Thermo Scientific, Rochester, N.Y.). Three-fold serial dilutions of 2× concentrated antibodies were prepared in FACs buffer (PBS+2% fetal bovine serum+ 0.02% azide) and were added to the cells in duplicate. The antibody solutions were incubated with cells for 1 hour on ice, protected from light. The cells were washed twice with FACs buffer and analyzed on the LSRII flow cytometer (BD BioSciences, San Jose, Calif.). KD values were determined with GraphPad Prism software (La Jolla, Calif.).

Murine anti-human NTB-A antibodies 11A1 and 26B7 were tested for binding to U-266 multiple myeloma cells and stable transfectants of 293-F17/hNTB-A isoform 4 and 293-F17/cynomolgus-NTB-A. Cells were plated at 2.5×105 cells/well in FACS buffer (PBS+2% fetal bovine serum+ 0.02% azide) and incubated with 2 μg/mL antibody for 45 minutes on ice. The cells were washed twice and stained with goat anti-mouse IgG-PE (Jackson ImmunoResearch, West Grove, Pa.) for 30 minutes, on ice and protected from light. Cells were again washed twice with FACs buffer and fixed with 500 μL of 1× PBS+1% paraformaldehyde. Stained cells were analyzed on the FACs Calibur flow cytometer (BD BioSciences, San Jose, Calif.).

TABLE 6

Affinity Measurements

| Antibody | Cell line | Kd (nM) Human NTB-A |
|---|---|---|
| 11A1 murine IgG1 antibody | Ramos | 0.13 |
| 26B7 murine IgG1 antibody | Ramos | 0.16 |

Example 8

In Vivo MM Xenograft Studies

NOD scid IL2 receptor gamma chain knockout (NSG) mice are used to develop disseminated cell line models of multiple myeloma in which tumor cells localize to the bone marrow compartment. Mice are implanted with 1 million MM.1R multiple myeloma cells or 5 million U-266 multiple myeloma cells, then dosed 5 days after tumor cell implant with anti-NTB-A antibody drug conjugates. The vcMMAE anti-NTB-A antibody drug conjugates loaded with 4 vcMMAE molecules are delivered to mice through intraperitoneal injection in a single dose at 1.0 and 3.0 mg/kg. Mouse serum is monitored by ELISA assay for levels of circulating lambda light chain Ig, secreted by the multiple myeloma tumor cells, every 2 to 3 weeks post antibody drug conjugate dosing. Mice in each study group are evaluated for signs of disease progression, and morbidity, and sacrificed on advanced signs of disease. Kaplan-Meier survival plots are generated for control and treatment study groups, and statistical analysis run to determine the significance of the observed antitumor activity at each ADC dose level versus vehicle control or nonbinding control ADC.

What is claimed is:

1. An isolated monoclonal antibody that specifically binds to human NTB-A (SLAMF6), wherein the antibody comprises:
   - a CDR-H1 amino acid sequence as shown in SEQ ID NO:5 or SEQ ID NO: 11;
   - a CDR-H2 amino acid sequence as shown in SEQ ID NO:6 or SEQ ID NO: 12;
   - a CDR-H3 amino acid sequence as shown in SEQ ID NO:7 or SEQ ID NO: 13;
   - a CDR-L1 amino acid sequence as shown in SEQ ID NO:8 or SEQ ID NO: 14;
   - a CDR-L2 amino acid sequence as shown in SEQ ID NO:9 or SEQ ID NO: 15; and
   - a CDR-L3 amino acid sequence as shown in SEQ ID NO:10 or SEQ ID NO: 16.

2. The antibody of claim 1, further comprising at least a portion of an immunoglobulin heavy chain constant region.

3. The antibody of claim 1, wherein the antibody further comprises VH and VL domains having amino acid sequences as respectively shown in residues 20-135 of SEQ ID NO: 1 and residues 21-140 of SEQ ID NO: 2.

4. The antibody of claim 3, wherein the antibody comprises a first polypeptide chain comprising the VH domain and a second polypeptide chain comprising the VL domain, the first polypeptide chain further comprising at least a portion of an immunoglobulin heavy chain constant region fused to the VH domain, and the second polypeptide chain further comprising at least a portion of an immunoglobulin light chain constant region fused to the VL domain.

5. The antibody of claim 2, wherein the heavy chain constant region is a mutant form of a natural human constant region having reduced binding to an Fcγreceptor relative to the natural human constant region.

6. The antibody of claim 2, wherein the heavy chain constant region is of an isotype selected from the group consisting of human isotypes IgG1, IgG2, IgG3, and IgG4.

7. The antibody of claim 1, wherein the antibody is conjugated to a cytotoxic or cytostatic agent.

8. The antibody of claim 4, wherein the heavy chain constant region is a mutant form of a natural human constant region having reduced binding to an Fcγreceptor relative to the natural human constant region.

9. A pharmaceutical composition comprising:
the antibody of claim 1; and
a pharmaceutically compatible ingredient.

10. An isolated murine monoclonal antibody comprising VH and VL domains having amino acid sequences as respectively shown in residues 20-135 of SEQ ID NO:1 and residues 21-140 of SEQ ID NO:2, or a chimeric or humanized form thereof.

11. An antibody drug conjugate comprising an antibody conjugated to a cytotoxic agent, wherein the antibody comprises VH and VL domains having amino acid sequences as respectively shown in residues 20-135 of SEQ ID NO:1 and residues 21-140 of SEQ ID NO:2, or a chimeric or humanized form thereof, and wherein the cytotoxic agent is vcMMAE.

12. A pharmaceutical composition comprising the antibody drug conjugate of claim 11.

\* \* \* \* \*